United States Patent
Duggan et al.

(10) Patent No.: US 9,668,718 B2
(45) Date of Patent: Jun. 6, 2017

(54) METHODS AND APPARATUS FOR TISSUE REMOVAL

(71) Applicant: THERAGENICS CORPORATION, Buford, GA (US)

(72) Inventors: John Duggan, Blackstone, MA (US); Hugh Tripp, Mansfield, MA (US); Thomas Johnson, Milford, NH (US)

(73) Assignee: Theragenics Corporation, Buford, GA (US)

( * ) Notice: Subject to any disclaimer, the term of this patent is extended or adjusted under 35 U.S.C. 154(b) by 0 days.

(21) Appl. No.: 15/186,492

(22) Filed: Jun. 19, 2016

(65) Prior Publication Data
US 2016/0324508 A1    Nov. 10, 2016

Related U.S. Application Data

(63) Continuation-in-part of application No. 14/123,394, filed as application No. PCT/US2012/040643 on Jun. 3, 2012, now Pat. No. 9,386,966.
(Continued)

(51) Int. Cl.
*A61B 5/00* (2006.01)
*A61B 10/02* (2006.01)
(Continued)

(52) U.S. Cl.
CPC .... *A61B 10/0275* (2013.01); *A61B 17/32053* (2013.01); *A61B 2010/0208* (2013.01);
(Continued)

(58) Field of Classification Search
CPC . A61B 10/02; A61B 10/0266; A61B 10/0275; A61B 2010/0208; A61B 2017/00867; A61B 2017/3405
See application file for complete search history.

(56) References Cited

U.S. PATENT DOCUMENTS

| | | |
|---|---|---|
| 2,516,492 A | 7/1950 | Turkel |
| 3,007,471 A | 11/1961 | McClure, Jr. |

(Continued)

FOREIGN PATENT DOCUMENTS

| | | |
|---|---|---|
| EP | 0852127 A1 | 7/1998 |
| EP | 1136039 A2 | 9/2001 |

(Continued)

OTHER PUBLICATIONS

Dennler, Samuel, International Preliminary Report on Patentability dated Jul. 10, 2009, PCT Application No. PCT/IB2008/000827, 11 pages, European Patent Office, Munich, Germany.
(Continued)

*Primary Examiner* — Max Hindenburg
(74) *Attorney, Agent, or Firm* — John J Brooks, III; John Brooks Law LLC

(57) ABSTRACT

A tissue removal apparatus and needle assembly for extracting a tissue portion from tissue or the like, the needle assembly comprising an inner tube having an interior cavity, an outer cannula having a proximal end, a distal end and an interior cavity, the interior cavity of the outer cannula having an interior diameter to slidably receive the inner tube and a collapsible section operably engaged with the inner tube and the outer cannula whereby a forward movement of a portion of the inner tube within the interior cavity of the outer cannula changes the collapsible section from a neutral position to a collapsed position to engage the tissue portion. In some embodiments, the outer cannula further comprises an aperture configured to allow a tissue portion from within the needle assembly to pass through or otherwise be expelled outside of the needle assembly.

20 Claims, 15 Drawing Sheets

Related U.S. Application Data

(60) Provisional application No. 62/181,320, filed on Jun. 18, 2015, provisional application No. 61/492,946, filed on Jun. 3, 2011.

(51) Int. Cl.
*A61B 17/3205* (2006.01)
*A61B 17/32* (2006.01)
*A61B 17/00* (2006.01)

(52) U.S. Cl.
CPC ............... *A61B 2017/00862* (2013.01); *A61B 2017/320064* (2013.01)

(56) References Cited

U.S. PATENT DOCUMENTS

| | | | |
|---|---|---|---|
| 3,175,554 | A | 3/1965 | Stewart |
| 3,605,721 | A | 9/1971 | Hallac |
| 3,683,892 | A | 8/1972 | Harris |
| 4,699,154 | A | 10/1987 | Lindgren |
| 4,785,826 | A | 11/1988 | Ward |
| 4,903,709 | A | 2/1990 | Skinner et al. |
| 5,462,062 | A | 10/1995 | Rubinstein et al. |
| 5,634,473 | A | 6/1997 | Goldenberg et al. |
| 5,655,542 | A | 8/1997 | Weilandt |
| 5,779,647 | A | 7/1998 | Chau et al. |
| 5,788,651 | A | 8/1998 | Weilandt |
| 5,885,226 | A | 3/1999 | Rubinstein et al. |
| 6,015,391 | A | 1/2000 | Rishton et al. |
| 6,110,128 | A | 8/2000 | Andelin et al. |
| 6,126,617 | A | 10/2000 | Weilandt et al. |
| 6,196,978 | B1 | 3/2001 | Weilandt et al. |
| 6,322,523 | B2 | 11/2001 | Weilandt et al. |
| 6,416,484 | B1 | 7/2002 | Miller et al. |
| 8,961,430 | B2 * | 2/2015 | Coonahan .......... A61B 10/0275 600/564 |
| 9,095,325 | B2 * | 8/2015 | Lubock .............. A61B 10/0275 |
| 9,095,327 | B2 * | 8/2015 | Weikel, Jr. ......... A61B 10/0275 |
| 9,241,692 | B2 * | 1/2016 | Gunday ............. A61B 10/0275 |
| 2008/0300507 | A1 | 12/2008 | Figueredo et al. |
| 2010/0106093 | A1 | 4/2010 | McGuckin, Jr. et al. |
| 2010/0106168 | A1 | 4/2010 | Selis |
| 2010/0160827 | A1 | 6/2010 | Buressiniani |

FOREIGN PATENT DOCUMENTS

| | | |
|---|---|---|
| EP | 1136039 A3 | 1/2003 |
| EP | 0852127 B1 | 4/2003 |
| WO | WO2005013831 | 2/2005 |

OTHER PUBLICATIONS

Dennler, Samuel, Written Opinion of the International Searching Authority dated Oct. 6, 2009, PCT Application No. PCT/IB2008/000827, 6 pages, European Patent Office, Munich, Germany.

Mayer-Martenson, E., International Preliminary Report on Patentability dated Nov. 10, 2005, PCT Application No. PCT/EP2004/008486, 15 pages, European Patent Office, Munich, Germany.

Mayer-Martenson, E., International Publication Bibliography Page with International Search Report dated Mar. 8, 2005, PCT Application No. PCT/EP2004/008486, 6 pages, World Intellectual Property Organization, Zurich, Switzerland.

Mayer-Martenson, E., Written Opinion of the International Searching Authority dated Mar. 7, 2005, PCT Application No. PCT/EP2004/008486, 6 pages, European Patent Office, Munich, Germany.

Dennler, Samuel, International Publication with International Search Report dated Sep. 10, 2008, PCT Application No. PCT/IB2008/000827, 22 pages.

Yoo Min Jeong, International Search Report and Written Opinion mailed Dec. 14, 2012, parent PCT Application No. PCT/US2012/040643, 12 pages, Korean Patent Office, Korea.

Max F. Hindenburg, Non-Final Office Action mailed Sep. 2, 2015, U.S. Appl. No. 14/123,394, 8 pages, United States Patent and Trademark Office, Alexandria VA.

Max F. Hindenburg, Final Office Action mailed Jan. 8, 2016, U.S. Appl. No. 14/123,394, 8 pages, United States Patent and Trademark Office, Alexandria VA.

Max F. Hindenburg, Notice of Allowance and Notice of Allowability mailed Mar. 14, 2016, U.S. Appl. No. 14/123,394, 4 pages, United States Patent and Trademark Office, Alexandria VA.

* cited by examiner

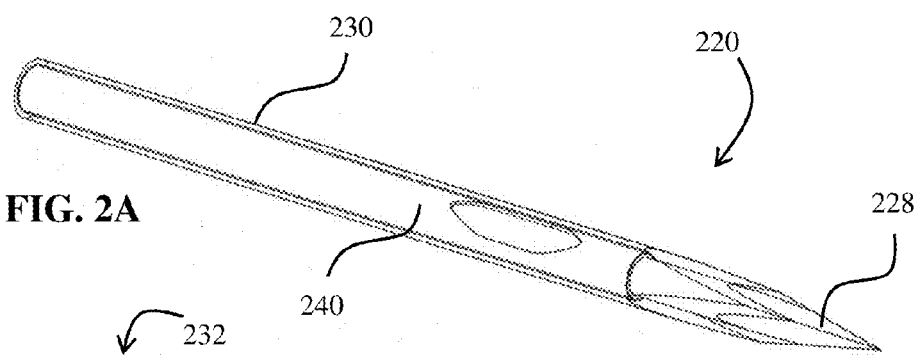
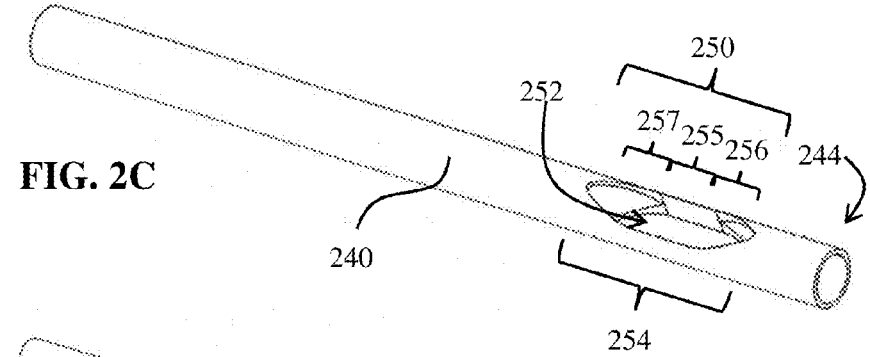
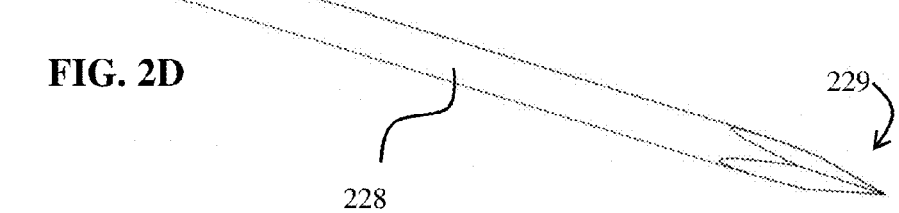

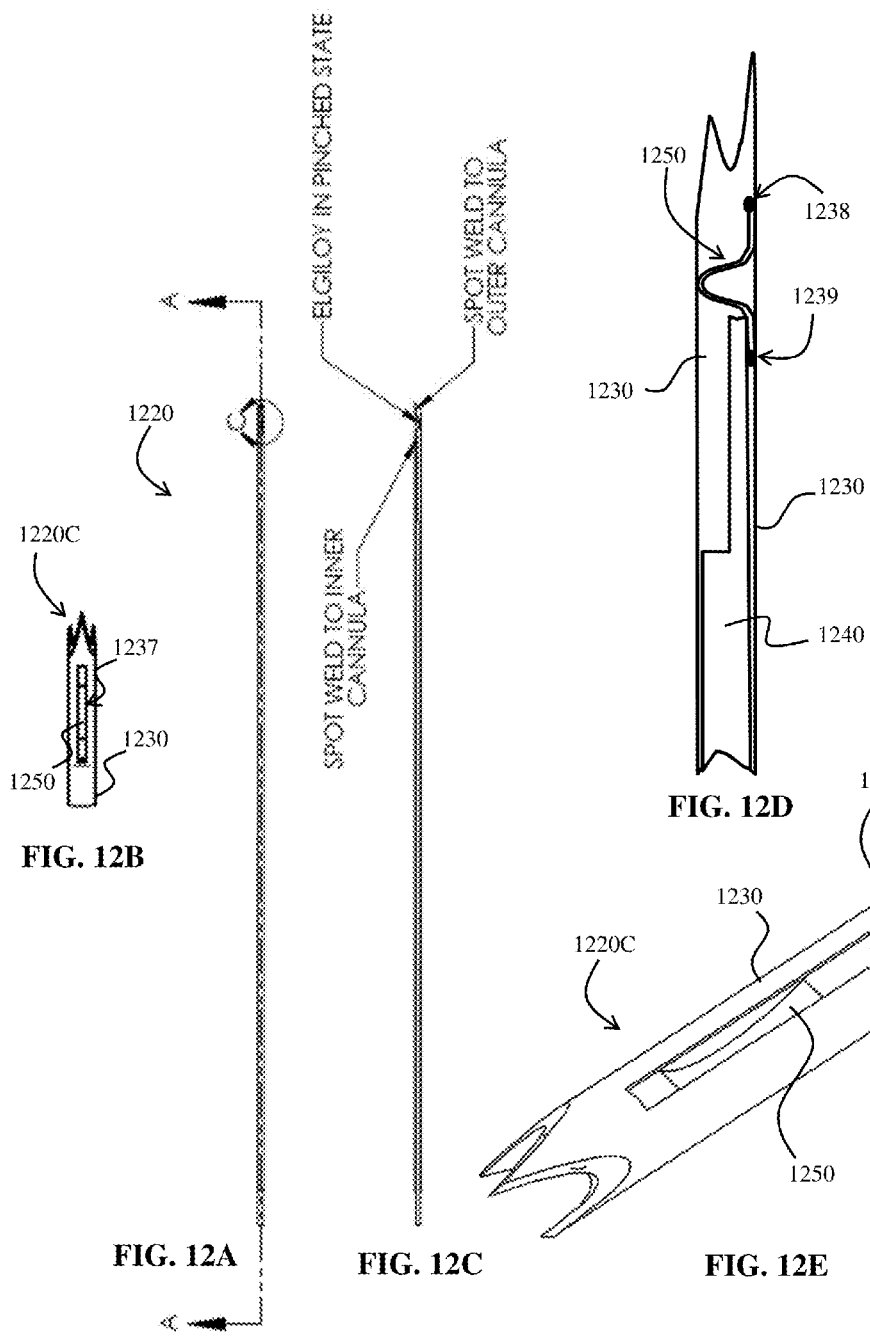

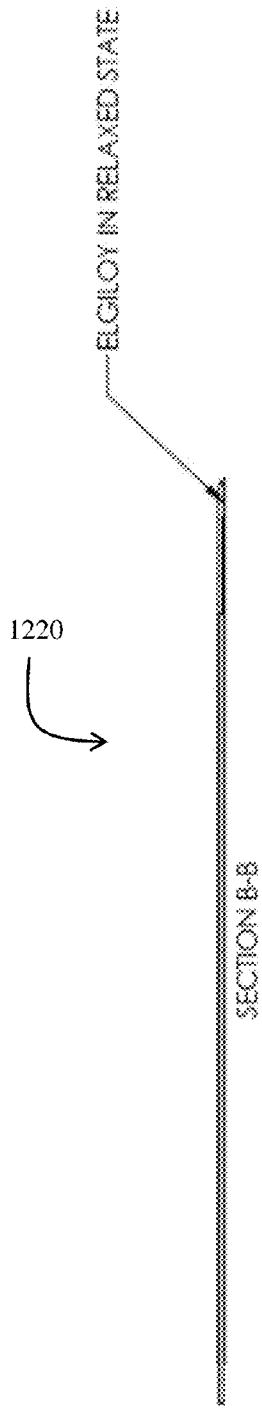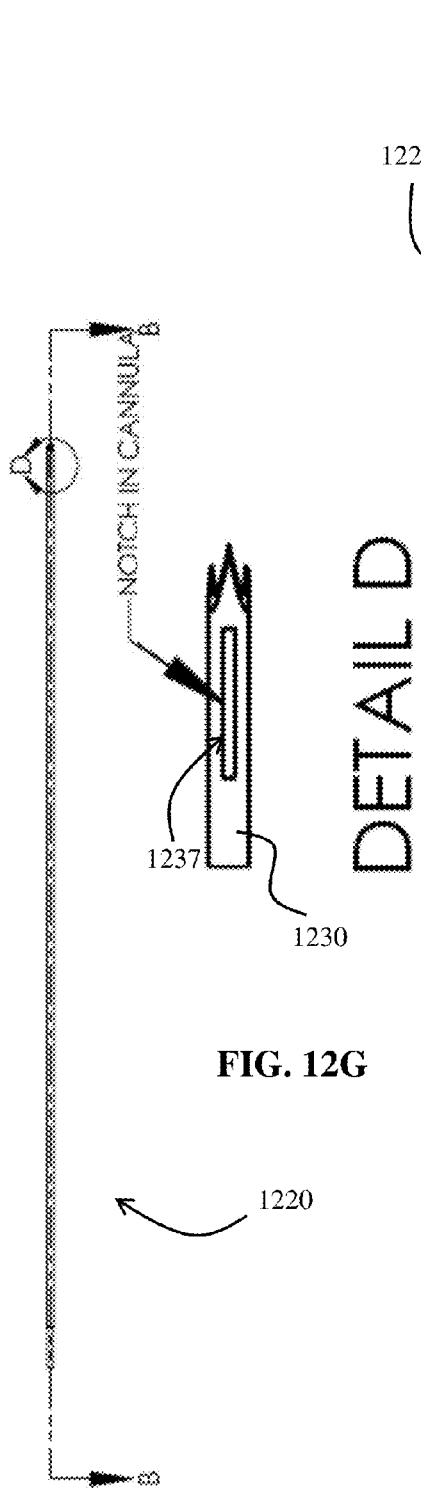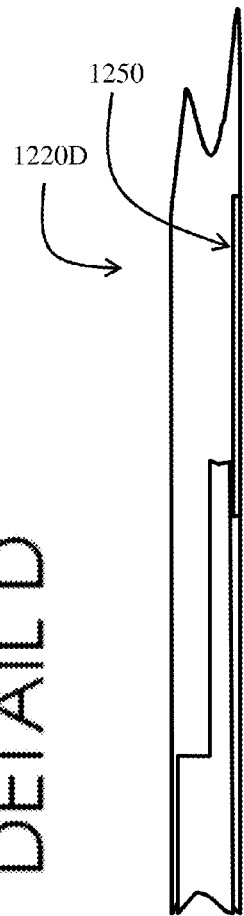
FIG. 12F
FIG. 12G
FIG. 12H

METHODS AND APPARATUS FOR TISSUE REMOVAL

CROSS-REFERENCE TO RELATED APPLICATIONS

This application claims benefit of U.S. Pat. App. No. 62/181,320 filed Jun. 18, 2015 entitled "METHOD AND APPARATUS FOR TISSUE REMOVAL"; this application is also a Continuation in Part of U.S. patent application Ser. No. 14/123,394 filed Dec. 2, 2013 entitled "METHOD AND APPARATUS FOR TISSUE REMOVAL"; U.S. patent application Ser. No. 14/123,349 is a 371 of PCT App. No. US2012/040643 filed Jun. 3, 2012 entitled "METHOD AND APPARATUS FOR TISSUE REMOVAL"; PCT App. No US2012/040643 claims benefit to U.S. patent application Ser. No. 61/492,946 filed Jun. 3, 2011 entitled "METHOD AND APPARATUS FOR TISSUE REMOVAL"; the entire content of these applications are herein incorporated by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

This invention relates to the removal of tissue samples or the like from humans or animals, in particular by excising a tissue portion from a tissue.

Biopsy devices are employed in modern medicine to collect tissue samples for examination typically for diagnosis of malignant or pre-malignant cell transformations indicating cancerous or pre-cancerous tumors. The procedure entails identifying the suspect tissue, bringing the biopsy device close to the tissue and depending on the type of action employed to cut and retain the required sample by firing a needle or cannula into the tissue and following up with a secondary action to sever and retain the sample tissue.

While there are multiple examples of biopsy devices currently being used to obtain tissue material for histological examination, the preservation of the sample with respect to tissue quality is sometimes compromised by the mechanical actions employed.

Some of the earlier Automated Core Biopsy Devices used a notched needle to obtain samples. However these yielded limited quantities due to the half round needle as shown in U.S. Pat. No. 4,699,154 to Radiplast AB, issued Oct. 13, 1987, also known as the "Tru-Cut" needle, which is herein incorporated by reference in its entirety. Others, in an attempt to retrieve full round core have utilized various means to cut and capture those round cores either by vacuum or a series of fingers cut in the wall of the cannula and depressed inward as shown in Patent Application Publication US 2008/0300507 to Stacy Figueredo et al. published Dec. 4, 2008 or in U.S. Pat. No. 5,655,542 to Anders Weilandt issued Aug. 12, 1997 and U.S. Pat. No. 6,322,523 to Anders Welandt issued Nov. 27, 2011 by means of an outer cannula with finger like projections that slide into windows cut in an inner tube. All publications and patents mentioned above are herein incorporated by reference in their entirety.

U.S. Pat. Pub. No. 20100160827, published Jun. 24, 2010, for U.S. patent application Ser. No. 12/594,835 having a §371 date of Jan. 27, 2010, to Odoardo Buressiniani ("Buressiniani"), which is herein incorporated by reference in its entirety, discloses a device having an outer cannula and an inner cannula having a plurality of ribs to engage a tissue sample.

U.S. Pat. No. 6,416,484, issued Jul. 9, 2002 to Michael E. Miller et al ("Miller"), which is herein incorporated by reference in its entirety, discloses a biopsy extractor having an outer cannula with a tapered end and an inelastically bendable portion to allow a head to sever and hold a tissue portion.

While these devices have worked to one degree or another, the issue of maintaining an intact tissue portion that is uncompromised by the engaging, cutting and retention means has not been addressed using the methods and means described herein.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented.

In one example embodiment a needle assembly is provided comprising an inner tube having an interior cavity, an outer cannula having a proximal portion, a distal portion and an interior cavity, the interior cavity of the outer cannula having an interior diameter to slidably receive the inner tube and an elastically collapsible leg operably engaged with the inner tube and the outer cannula whereby a forward movement of a portion of the inner tube within the interior cavity of the outer cannula changes the elastically collapsible leg from a neutral position to a collapsed position. In some embodiments, the elastically collapsible leg is formed from an elgiloy. In some embodiments, the elastically collapsible leg is formed from a super elastic material. In some embodiments, the elastically collapsible leg further comprises a cutting edge. In some embodiments, an interior cavity wall defines the interior cavity of the outer cannula, the elastically collapsible leg further comprises a cutting edge and the collapsed position positions the cutting edge across a portion of the interior cavity of the outer cannula and proximal to a portion of the interior cavity wall of the outer cannula. In some embodiments, the elastically collapsible leg is further configured to deform to the collapsed position by the forward movement of a proximal section of the elastically collapsible leg and by a restrained movement or lack of movement of a distal section of the elastically collapsible leg. In some embodiments, a smaller diameter portion of the interior cavity of the outer cannula defines a step configured to restrict movement of the distal section of the elastically collapsible leg. In some embodiments, the inner tube has a distal portion and a body portion and the elastically collapsible leg is coupled to the distal portion and the body portion of the inner tube. In some embodiments, the elastically collapsible leg is coupled to the distal portion of the inner tube by a first weld and the elastically collapsible leg is coupled to the body portion of the inner tube by a second weld. In some embodiments, the elastically collapsible leg is coupled to a distal portion of the inner tube and a distal portion of the outer cannula. In some embodiments, the elastically collapsible leg is coupled to the distal portion of the inner tube by a first weld and the elastically collapsible leg is coupled to the distal portion of the outer cannula by a second weld. In some embodiments, the needle assembly further comprises a first cam coupled to the proximal portion of the inner tube and a second cam coupled to the proximal portion of the outer cannula. In some embodiments, the needle assembly further comprises a holder assembly comprising a first spring and a second spring, the first spring configured to provide a first force on the first cam and the second spring configured to provide a second force on the second cam. In some embodiments, the needle assembly further comprises at least one additional collapsible leg. In some embodiments, the needle assembly further comprises a plunger slidably disposed within the interior cavity of the inner tube. In some embodiment, the needle assembly further comprises a first cam coupled to the proximal portion of the inner tube, a second cam coupled to the proximal portion of the outer cannula, a third cam coupled to the plunger, a handle comprising a first spring and a second spring, the first spring configured to provide a first force on the first cam, the second spring configured to provide a second force on the second cam and the third cam configured to provide a third force on the plunger.

In one example embodiment, the needle assembly comprises an inner tube for use with a biopsy needle, the inner tube comprising an inner tube having an interior cavity; an elastically collapsible leg having a distal section, a proximal section and a middle section and the elastically collapsible leg configured to deform to a collapsed position by a forward movement of the proximal section of the collapsible leg within an interior cavity of the biopsy needle. In some embodiments, the elastically collapsible leg is further configured to deform to the collapsed position by the forward movement of the proximal section of the collapsible leg and by a restrained movement or lack of movement of the distal section of the collapsible leg. In some embodiments, the elastically collapsible leg is formed from an elgiloy or from a super elastic material. In some embodiments, the elastically collapsible leg further comprises a cutting edge. In some embodiments, the interior cavity of the outer cannula is defined by an interior cavity wall, the elastically collapsible leg further comprises a cutting edge and the collapsed position of the elastically collapsible leg positions the cutting edge across a portion of the interior cavity of the inner tube and against a portion of the interior cavity wall of the inner tube. In some embodiments, the elastically collapsible leg is coupled to a distal portion of the inner tube and a distal portion of the biopsy needle. In some embodiments, the elastically collapsible leg is coupled to the inner tube with a weld.

In one example embodiment, a tissue removal assembly is provided comprising an outer cannula, an inner tube slidably received in the outer cannula, a holder assembly configured to provide a forward force on the inner tube and a restraining force on the outer cannula and a collapsible section coupled to the inner tube and the outer cannula whereby the forward force on the inner tube and the restraining force one the outer cannula collapses the collapsible section into a collapsed position. In some embodiments, the collapsible section is coupled to the inner tube with a weld. In some embodiments the outer cannula further comprises a proximal portion coupled to an outer cannula cam to receive the restraining force, the inner tube further comprises a proximal portion coupled to an inner tube cam to receive the forward force and the holder assembly comprising a force element configured to automatically provide the forward force to the inner tube cam. In some embodiments, the tissue removal assembly further comprises a cocking element configured to receive a cocking force and return the needle assembly to a ready configuration, a plunger slidably received in the inner tube and the plunger dimensioned to have a length whereby the plunger expels a tissue in the inner tube when the needle assembly is in the ready configuration. In some embodiments the outer cannula further comprises a proximal portion coupled to an outer cannula cam to receive the restraining force, the inner tube further comprises a proximal portion coupled to an inner tube cam to receive the forward force and the forward force is a manually applied force. In some embodiments, the tissue removal assembly further comprises a plunger slidably received in the inner tube and the plunger dimensioned to have a length whereby the plunger can be received in a majority of the inner tube and expel a tissue.

In one example embodiment, a method of tissue removal is provided comprising the steps of positioning a needle assembly in a tissue, engaging a tissue portion, and withdrawing the tissue portion from the tissue. In some embodiments the step of engaging a tissue portion further comprises, applying a forward force to the inner tube, applying a retrograde force to the outer cannula and collapsing a collapsible section whereby the collapsible section engages the tissue portion in an inner tube. In some embodiments, the step of withdrawing the tissue portion further comprises withdrawing the needle assembly from the tissue, applying a retrograde force on the collapsible section, disengaging the tissue portion and removing the tissue portion from the needle assembly. In some embodiments, the step of removing the tissue portion from the needle assembly comprises receiving a plunger in a portion of the inner tube expelling the tissue portion. In some embodiments, the method of further comprises reconfiguring the needle assembly into a ready configuration.

In some embodiments, the needle assembly comprises an inner tube having an interior cavity, an outer cannula having a proximal portion, a distal portion and an interior cavity, the interior cavity of the outer cannula having an interior diameter to slidably receive the inner tube and a collapsible leg operably engaged with the inner tube and the outer cannula whereby a forward movement of a portion of the inner tube within the interior cavity of the outer cannula changes the collapsible leg from a neutral position to a collapsed position.

In some embodiments, the needle assembly further comprises an aperture extending through an interior cavity wall from an interior cavity wall inner surface to an exterior surface of the interior cavity wall of the outer cannula whereby a tissue may be expelled from the interior cavity of the outer cannula through the aperture. In some embodiments, the aperture extends through the interior cavity wall from the interior cavity wall inner surface to the exterior surface of the interior cavity wall of the outer cannula whereby a first tissue portion comprising a sample portion may be retained in the interior cavity of the outer cannula and a second tissue portion comprising a non-sample portion may be expelled from the interior cavity of the outer cannula through the aperture. In some embodiments, the aperture extends through the interior cavity wall of the outer cannula whereby a tissue may be expelled from the interior cavity of the outer cannula and under the collapsible leg through the aperture. In some embodiments, the aperture extends through the interior cavity wall of the outer cannula wherein the aperture is positioned under the collapsible leg when the inner tube and the collapsible leg are received in the interior cavity of the outer cannula. In some embodiments, the aperture shape comprises one selected from the group consisting of a rectangle, an oval and a rectangle with rounded or otherwise curved edges. In some embodiments, the collapsible leg comprises a separately manufactured element coupled to the inner tube. In some embodiments, the collapsible leg is coupled to the distal portion of the inner tube by a first weld and to the distal portion of the outer cannula by a second weld. In some embodiments, the needle assembly further comprises a first cam coupled to the proximal portion of the inner tube and a second cam coupled to the proximal portion of the outer cannula. In some embodiments, the collapsible leg is an elastically collapsible leg. In some embodiments, the needle assembly is configured to be reused to remove a plurality of tissue portions.

Other embodiments, objects, advantages and benefits are accomplished according to the devices, assemblies and methods described herein.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific example embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 2A-2D are multiple perspective illustrations of one embodiment of the components of a needle assembly;

FIGS. 12A-12H show different views of portions of an example embodiment of a needle assembly having an aperture;

DETAILED DESCRIPTION OF THE INVENTION

Methods and apparatus for tissue removal will now be described in detail with reference to the accompanying drawings. It will be appreciated that, while the following description illustrates methods and an apparatus that removes tissue portions from the human body, the systems and methods disclosed herein have wide applicability. Notwithstanding the specific example embodiments set forth below, all such variations and modifications that would be envisioned by one of ordinary skill in the art are intended to fall within the scope of this disclosure.

Figure 1:
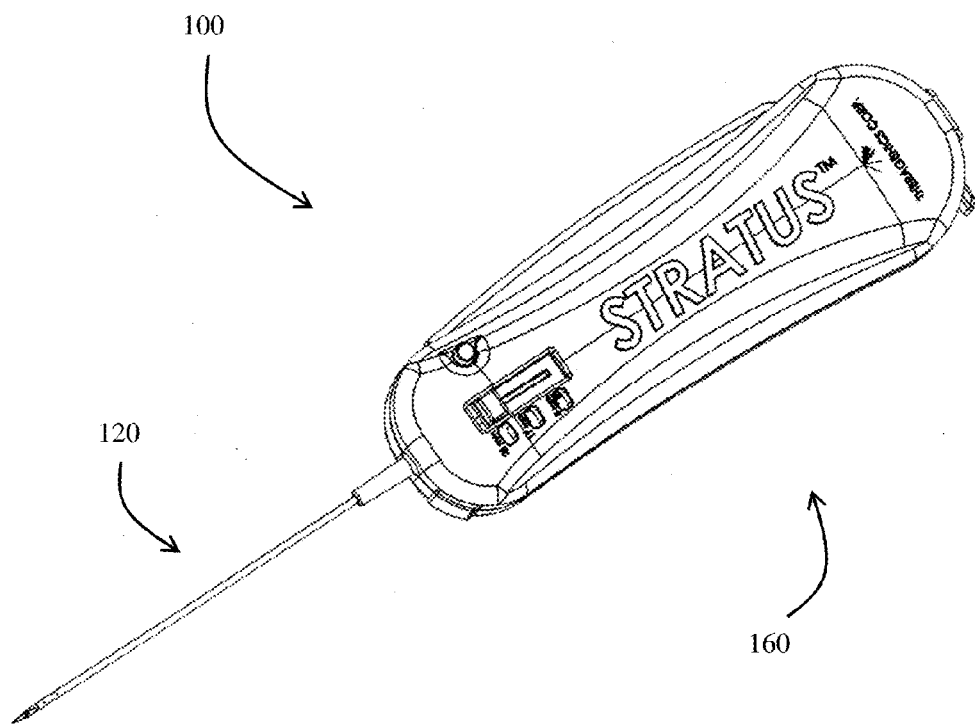
FIG. 1 is a perspective illustration of one embodiment of a tissue removal apparatus.

One Embodiment of the Tissue Removal Apparatus:

As shown in FIG. 1, one embodiment of the tissue removal apparatus 100 generally comprises a needle assembly 120 and a holder assembly 160.

In one example embodiment, the needle assembly 120 generally comprises an inner tube, an outer tube having an interior cavity with a diameter to slidably receive the inner tube and a collapsible section operably engaged with the inner tube and the outer cannula whereby a forward movement of a portion of the inner tube within the interior cavity of the outer cannula changes the collapsible section from a neutral position to a collapsed position.

The inner tube, a substantially tubular part, also called a cannula or inner cannula, has an interior cavity and a distal portion with a distal end configured to penetrate a tissue. The outer cannula or outer tube may be constructed from a single piece or it may be constructed using multiple parts such as the distal end having a cutting edge being welded to a second tube. In some embodiments, the second tube may have a slightly larger inside diameter (ID) to create a stepped edge if necessary. Slidably disposed within the outer cannula is a second substantially tubular part, also called a tube or an inner tube, having an interior to receive a portion of tissue when the tissue is penetrated by the outer cannula and the inner tube. The inner tube may be constructed from a single piece of material or it may be constructed from multiple parts such as a pusher tube from a proximal end towards a distal portion with a distal end.

In some embodiments, the needle assembly also comprises a collapsible section configured to separate a tissue portion received in the inner tube when the tissue is penetrated by the cannula. In one embodiment, the collapsible section is part of the inner tube comprising a short length of elastic material, at its distal portion with the section configured to create the collapsible section. In one embodiment, the collapsible section has a projecting section configured to move into the inner tube interior when the collapsible section changes from a neutral position to a collapsed position whereby the projection section may engage a portion of the tissue portion inserted through the proximal end of the inner tube and in the interior cavity of the inner tube. As used herein, the proximal and distal locations typically define relative locations where a proximal location is a location closer to the user than the distal location during use.

Referring again to FIG. 1, the tissue removal apparatus may include a holder assembly 160. The holder assembly 160 provides a place for the user to grip the apparatus and maneuver the needle assembly 120 like a handle. The holder assembly may also include elements to interoperate with the needle assembly such as having a trigger mechanism providing a means to trigger the needle assembly and elements to provide a means to separate the tissue portion from the tissue.

This embodiment of the needle assembly also includes a trocar needle which can be received and held in the inner tube interior.

As described below, the apparatus may also include a cocking mechanism to cock the trigger mechanism and the apparatus may also include elements to remove the tissue portion from the interior of the inner tube when needed.

Having described the general functions of one embodiment of a tissue removal apparatus, for further illustration purposes and not for limitation, one embodiment of the needle assembly will be described in more detail with reference to FIGS. 2A-6B.

As shown in FIG. 2A, one embodiment of a tissue removal apparatus comprises a needle assembly where the needle assembly 220 comprises an outer cannula 230, an inner tube 240 and a collapsible section to separate a tissue portion. Shown in FIGS. 2A and 2D is an optional trocar needle 228.

Detailed in the embodiment of FIG. 2B (showing interior and exterior edges), the outer cannula 230 extends from a proximal or head portion 232 to a distal portion 234. The head portion 232 of the outer cannula is shaped to interoperate with other apparatus elements such as a holder assembly. The end of the outer cannula distal portion 234 can be of any shape, but may be sharpened with a cutting edge or otherwise shaped to assist in penetrating the tissue. The interior cavity of the outer cannula is defined by interior cavity walls. This embodiment of the outer cannula also incorporates a sharp edge, here a castellated cutting edge 236 at its distal end to assist the outer cannula 230 penetrating the tissue. In this embodiment, the outer cannula 230 has an interior shaped to retain the inner tube and a more restricted, smaller, inner diameter located proximal to the distal end such that the distal end of the inner tube will restrict the movement of the inner tube by engaging the inner tube's outer diameter. In one embodiment, the restricted inner diameter or smaller diameter portion defines an inner step 238 to restrict further distal movement of the distal end of the inner tube and a distal section of the collapsible section. The outer cannula 230 can be made from any rigid surgical material such as but not limited to stainless steel. Dimensions of the outer cannula 230 can be any dimension based on the user's preference or on the type of procedure that the assembly will be used for. Suitable sizes by gauge size and inside diameter (ID) and outside diameter (OD) typically include but are not limited to 11 gauge [(0.120" OD×0.100" ID), (3.048 mm OD×2.54 mm ID)], 12 gauge [(0.109" OD×0.091" ID), (2.769 mm OD×2.311 mm ID)], 14 gauge [(0.083" OD×0.072" ID), (2.108 mm OD×1.829 mm ID)], 16 gauge [(0.065" OD×0.055" ID), (1.651 mm OD×1.397 mm ID)], 18 gauge [(0.050" OD×0.042" ID), (1.27 mm OD×1.067 mm ID)] and 20 gauge [(0.028" OD×0.020" ID), (0.711 mm OD×0.508 mm ID)]. The lengths of the outer cannula 230 depend on size and application but example embodiments include lengths of about 10 cm, 15 cm, 20 cm and 25 cm. Although the above embodiment has a stepped interior diameter restrict the movement of the inner tube, other embodiments may use other elements to restrict the movement such as ridges, notches, ribs, welds or any other type of protrusions or restrictions to effectively reduce the inner diameter of the cannula at that point.

Detailed in FIG. 2C, one embodiment of the inner tube 240 is a thin wall cannula or tube with a super elastic or elastic collapsible section 250 that has a bias to collapse in a pre-defined manner. The collapsible section 250 is positioned near the end of the distal portion 244 of the inner tube 240. The collapsible section 250 may be defined by a cut configuration of partially removed inner tube wall portions 252 such that a non-removed wall portion (connecting section 254) forms a strip of material that will deflect into a projecting section (shown in FIGS. 3A-3C), such as in a knee like shape, when some pressure is applied to it and then return to its original shape once the compressive force is released. The inner tube 240 can be made from any elastic or superelastic surgical material including, but not limited to, metals, metal alloys such as nickel titanium alloys known to be shape-memory metals which are sold and manufactured under the trademark "Nitinol," and rigid or semi-rigid plastics. It is also anticipated that new materials, as they are developed, will be useful such as but not limited to elgiloy. The inner tube is sized to fit within the inside diameter for the outer cannula yet still have a suitably sized interior to receive tissue portions. Examples of suitable lengths for the inner tube include lengths similar to those of the outer cannula listed above and outside diameters slightly smaller than the inside diameter of the outer cannula (excluding the stepped diameter). The inside and outside diameter of the inner tube 240 is a function of the gauge size with a wall thickness of between 0.002 to 0.0035 inches (0.0508 to 0.089 mm). Suitable sizes by gauge size include but are not limited to 11 gauge [(0.099" (inches) OD×0.093" ID). (2.525 mm OD×2.362 mm ID)], 12 gauge [(0.090" OD×0.084" ID), (2.286 mm OD×2.133 mm ID)], 14 gauge [(0.071" OD×0.065" ID), (1.803 mm OD×1.651 mm ID)], 16 gauge [(0.054" OD×0.050" ID), (1.372 mm OD×1.27 mm ID)], 18 gauge [(0.041" OD×0.038" ID), (1.041 mm OD×0.965 mm ID)] and 20 gauge [(0.027" OD×0.023" ID), (0.6858 mm OD×0.584 mm ID)].

The collapsible section 250 possesses characteristics of being able to bend, deform or otherwise collapse in deflection from a neutral position to a collapsed position but will return to its original neutral position shape without taking a set. In its normal, neutral position prior to firing or collapsing, but in a ready state, the inner tube and the collapsible section 250 has a generally full round inside diameter allowing the outer cannula and the inner tube to pass over a trocar needle which may be the inner most member of the needle assembly and the trocar may be stationary relative to the cannula and the inner tube.

The modification of the inner tube walls by cutting specific shapes and the alignment of those shapes may create an interaction of the shapes with the tissue portion to engage or sever and hold the portion in place until such time as it can be removed by reversing the process. Cutting may be made by methods such as etching, laser cutting, chemical cutting, water jet cutting or machining. The cutting may be made directly to a tube or the cutting may be made to a sheet of elastic material where that sheet will later be welded or otherwise shaped into a tube.

Other enhancements can be made to the collapsible section 250 to bias the collapse. For example, the walls of the tube may be etched, cut or machined to create points, like inflection points, where the material and the tube is more likely to bend. Methods of creating these points may be with the use of etching such as laser or chemical etching or cutting away a certain thickness of the using through such means as laser cutting, chemical cutting, water jet cutting or machining.

In addition to cutting or etching to add characteristics to the inner tube, methods similar to those described in U.S. Patent Pub. No. US2010/0106093 to McGluckin et al., published Apr. 29, 2010, which is herein incorporated by reference in its entirety, can be used. For example, bends can be formed in the Nitinol tube by either deforming the inner tube under extreme heat for a prescribed period of time or by cold working the inner tube by applying mechanical stress to deflect the inner tube.

Referring back to the embodiment of FIG. 2C, the collapsible section 250 is defined by the section of the tube having a connecting section 254 and a removed portion 252 of the tube wall. The connecting section 254 of the tube wall comprises a middle or projecting section 255, a distal section 256 and a proximal section 257. In this embodiment, the connecting section 254 is created by removing a portion of the inner tube wall. The size of the removed portion 252 can be any size to increase the tendency for the connecting section 254 to bend when a force is placed on either end portions of the inner tube. Consistent with the example shown, the removed portion can be any size that still allows a portion of the width of the connecting section to define a projecting section 255 that can engage the tissue portion in the tube interior and pull the portion when the needle assembly is removed from the tissue. A suitable range of dimensions for the width (or partial outside circumference) of the projecting section 255 is about forty (40) to eighty (80) percent of the inside diameter of the tube with a preferable dimension of about fifty (50) to sixty (60) percent of the ID. This width may be provided by a single projecting section or it may be provided by the cooperation of multiple projecting sections. The overall length of the collapsible section varies with the gauge size of the tube. The profile length can be any suitable length, with lengths from 0.120 inches (3.048 mm) for a 20 gauge to 0.300 inches (7.6199 mm) for an 11 gauge tube as suitable examples. If a Nitinol segment of the inner tube 240 is used to provide the features of the collapsible section, the Nitinol segment will vary according to the gauge size. One example embodiment of the Nitinol segment may be typically in the range of 0.150 to 0.500 inches (3.810 to 12.7 mm) long.

Although embodiments of the collapsible section 250 include those that are integral to the inner tube, it is also understood that the collapsible section 250 may be a separate element coupled to the inner tube or it may be a separate element that is dimensioned so that it interoperates within the outer cannula and the inner tube and provide the functional features as if it were integral to the inner tube. For example, the collapsible section 250 may be a separate, short tube with OD and ID similar to the inner tube and removed portions providing the bias to collapse and this collapsible section fits between the stop of the outer cannula and inner tube so that forces on the inner tube are translated to the collapsible section and it collapses.

As operationally described below, the needle assembly may further include other elements to interoperate with the collapsible section. In this embodiment, the inner tube and the outer cannula interoperate to help separate the tissue portion. As shown in FIGS. 2B and 2C, the outer cannula 240 has a stepped insider diameter 238 smaller than the OD of the inner tube 240 so that it retains or restricts the inner tube 240 and prevents it from moving out of the distal end of the outer cannula 230. When a force is put on the proximal portion 242 of the inner tube, because the distal portion 244 cannot move due to the step 238, this force is translated to urge the collapsible section 250 to collapse to a collapsed position.

Figure 3A:
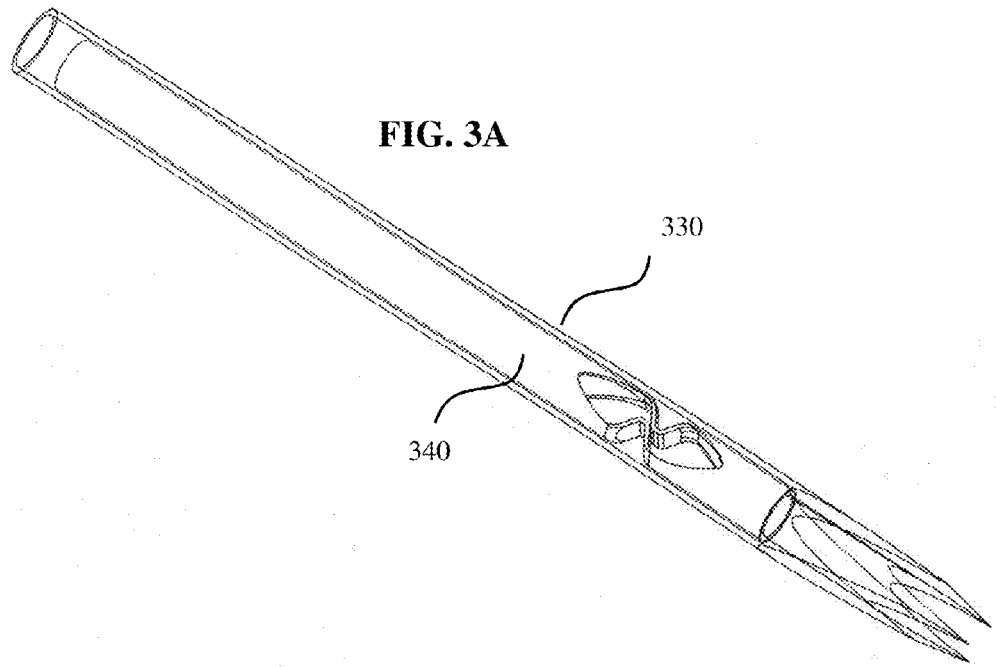
FIGS. 3A-3C illustrate of one embodiment of an inner tube showing different perspective views of the collapsible section in a collapsed position.
Figure 3B:
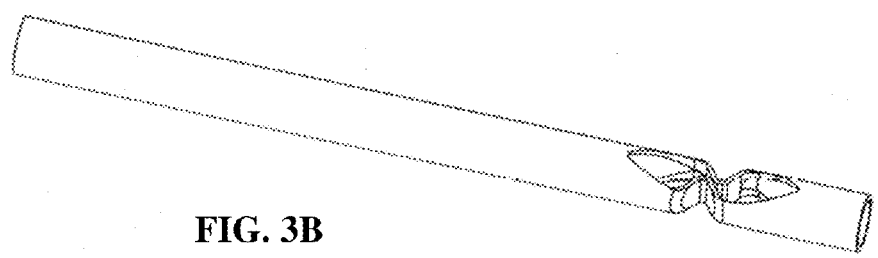
Figure 3C:
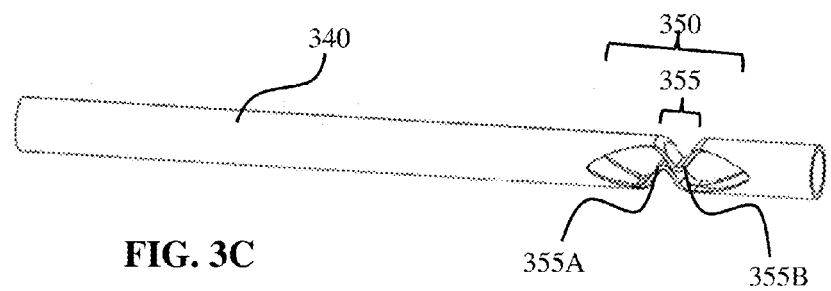

FIG. 3A illustrates the collapse of the collapsible section within the outer cannula 330. FIGS. 3B-3C show different views of a collapsed collapsible section 350 outside of the inner tube. As shown in FIG. 3C, when the collapsible section 350 collapses, the projecting sections 355A and 355B are urged and displaced into the interior of the inner tube 340 engaging whatever material may in the inner tube at the time, such as a tissue portion. The projecting sections 355A and 355B may sever the tissue portion or it may frictionally engage the tissue portion so that it can be severed by movement of the inner tube 340 and collapsible section 350 such as through withdrawal of the needle assembly from the tissue. As shown, the two offset projecting sections 355A and 355B form an "S" shaped constriction within the interior of the inner tube 340. For embodiments that include a trocar needle, the trocar needle is usually positioned well distal to the collapsible section 350 when a tissue portion is to be placed into the cavity of the inner tube 340.

As described above, the collapsible section 350 can be enhanced with attributes to further promote the collapsing of the collapsible section 350. For example and not for limitation, inflection points may be etched or cut into the wall of the inner tube 340 to help bias the projection of the projecting sections. Suitable inflection points for the configuration shown in FIG. 3C would include etchings or cuts made on the inside of the wall of the inner tube 340 at either end of the projecting section 355 and an etching or cut made on the outside of the inner tube wall at the center so that the projecting sections 355A and 355B create a "knee" like protrusion. Other configurations of etching or partial cutting of the inner tube 340 to enhance its collapse are also suitable. As described above, the inflection points may be made directly to the inner tube or they may be made on material that will be later shaped to create the inner tube 340.

Figure 4:
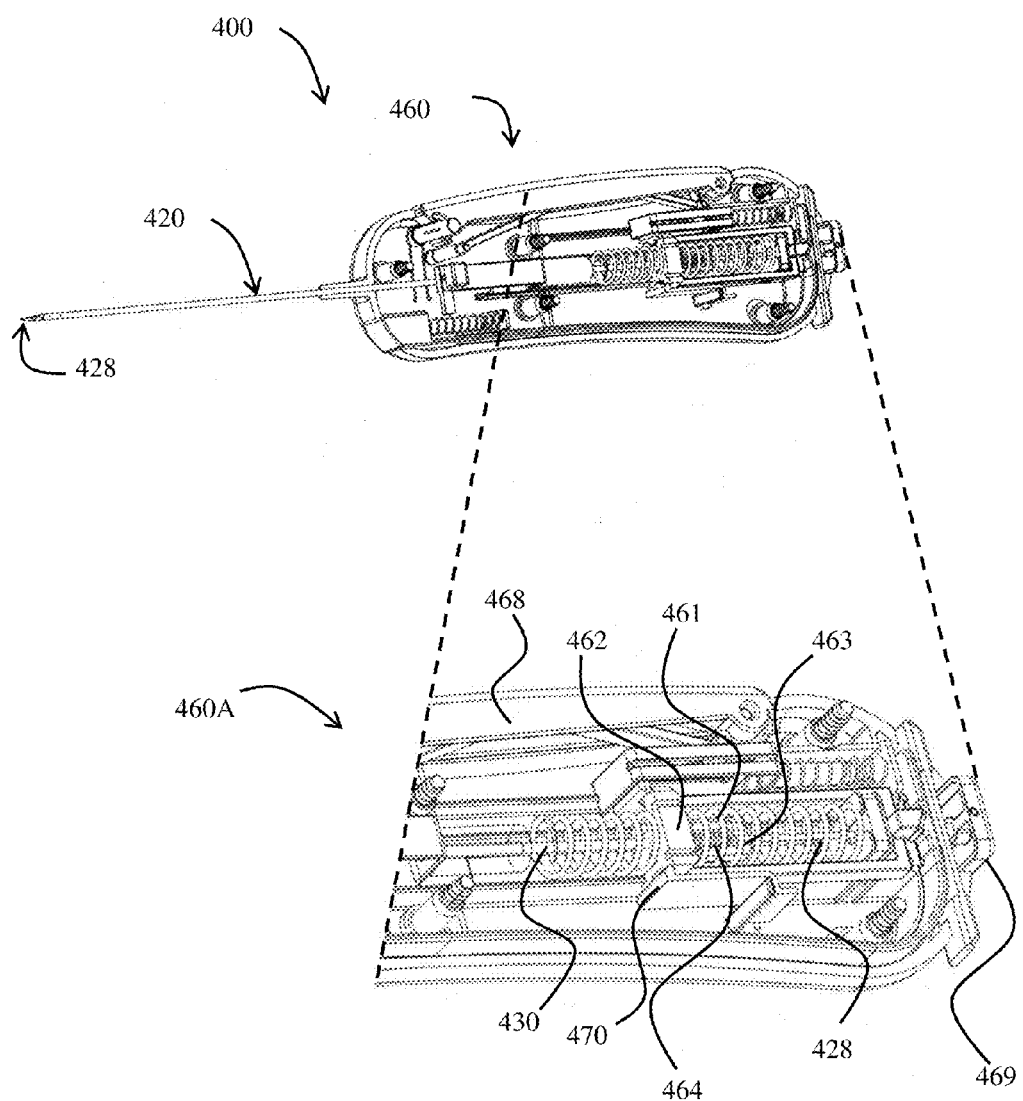
FIG. 4 is a perspective illustration of one embodiment of a tissue removal apparatus with the holder assembly partially exposing elements of the holder assembly.

An example embodiment of a needle assembly in a tissue removal apparatus is shown in FIG. 4. In this embodiment, the apparatus 400 integrates the needle assembly 420 with a holder assembly 460 and a trocar needle 428.

Referring to the example embodiment of FIG. 2A, the trocar needle 228 may be a rigid elongated rod positioned within the inner tube as the inner most member of the needle assembly. The trocar needle 228 may be used with the holder assembly to position the distal end of the needle assembly near the tissue to be removed. As detailed in FIG. 2D, preferably, the trocar 228 has a cutting or sharpened tip 229 to ease positioning of the apparatus and can be secured to the holder assembly so that the user can manipulate the trocar needle and the needle assembly with the holder assembly. In the embodiment shown in FIG. 4, the trocar needle 428 is stationary relative to the holder assembly 460 as opposed to the inner tube and outer cannula that are able to move relative to the holder assembly 460.

As shown in FIG. 4, this embodiment of the holder assembly 460 includes a trigger mechanism and elements to assist separating the tissue portion. The trigger mechanism comprises a force element interoperating with the outer cannula and inner tube of the needle assembly 420. The force element axially displaces the cannula and inner tube in a distal direction relative to the holder assembly and may also be structured and arranged for substantially consecutive axial displacement of the cannula and the inner tube in combination, and of the inner tube only. In an example embodiment, as shown in the holder assembly 460A, which is a blown up partial view of holder assembly 460, the force element has a first and second force element. In the embodiment shown, the first force element comprises a first spring 461. This force element operationally engages a first cam 462 coupled to the outer cannula. The first spring 461 engaging the first cam 462 displaces both the outer cannula 430 and the inner tube (within the cannula) by engaging their proximal ends or other proximal portions. A second force is provided that displaces the proximal portion of the inner tube. In this embodiment, the second force is applied to the inner tube by the momentum of the inner tube and the inner tube cam 463 as they are advanced with the outer cannula 430 by the first force element. This momentum urges the inner tube to advance even as the movement is restricted by the distal portion of the outer cannula 430. The displacement of the inner tube proximal or head portion by the second force only enables the proximal portion of the inner tube (pusher section) to be displaced, and with the distal portion of the inner tube restricted, it causes the collapsible section of the inner tube to collapse within the inner tube cavity. When a portion of tissue is within the inner tube cavity beyond the collapsible section (towards the head end), that portion of tissue is engaged by the projecting section so that it can be separated from the rest of the tissue and held within the inner tube so that is can be withdrawn from the rest of the tissue. Also shown is a buffer spring 464 to buffer the movement of the inner cannula relative to the outer cannula which may also provide a retrograde force on the inner cannula cam.

In this embodiment, the trocar needle 428 is coupled to the housing of the holder assembly 460A. The trocar needle 428 does not move relative to the holder assembly 460, but the outer cannula and inner tube may be moved relative to the trocar needle 460.

The second force above may be any force to displace the proximal portion of the inner tube when the outer cannula stops advancing and may interoperate with other apparatus elements to retain the collapsible section in a collapsed position. One suitable force is the inertia of the inner tube and inner tube cam to collapse the collapsible section where it will engage the tissue portion, rebound (not collapsed) and friction with the tube inner walls hold the tissue in place until the tissue portion is pushed out. Another example of a suitable force is a manually applied force to the inner tube or the inner tube cam. Embodiments may also include a latching mechanism to engage the tube once the tube advances to a point where it has collapsed the collapsible section and the latching mechanism holds the inner tube in position until it is unlatched when the assembly pushes out the tissue portion. Other embodiments may include a push rod or plunger activated by the cannula stopper and pushing the tube forward and held in place by a spring until the assembly pushes out the tissue portion.

The holder assembly 460 may also include a cocking mechanism and a removal mechanism to remove the tissue portion from the interior cavity of the inner tube. In this embodiment, the cocking mechanism may comprise a cocking handle 468 that operates to pull back the extended outer cannula cam 462 back to engage a latch 470 and retain the needle assembly 420 in the ready configuration for reuse. The removal mechanism in this embodiment is provided by the trocar needle 428 that maintains its position in relation to the holder assembly 460 while the needle assembly 420 is cocked and therefore pushes any tissue portion out of the inner cannula.

Other embodiments of collapsible sections of the inner tube are shown in FIGS. 5A-6B.

Figure 5A:
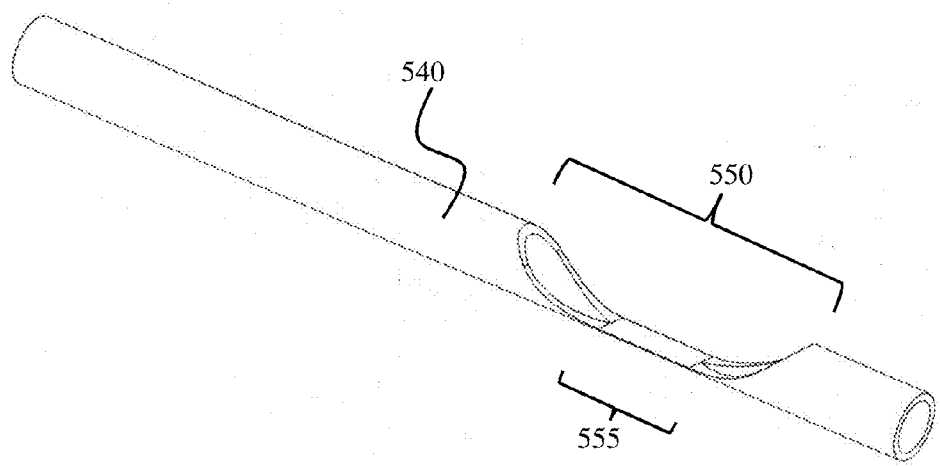
FIG. 5A is a perspective illustration of an alternative embodiment of an inner tube.
Figure 5B:
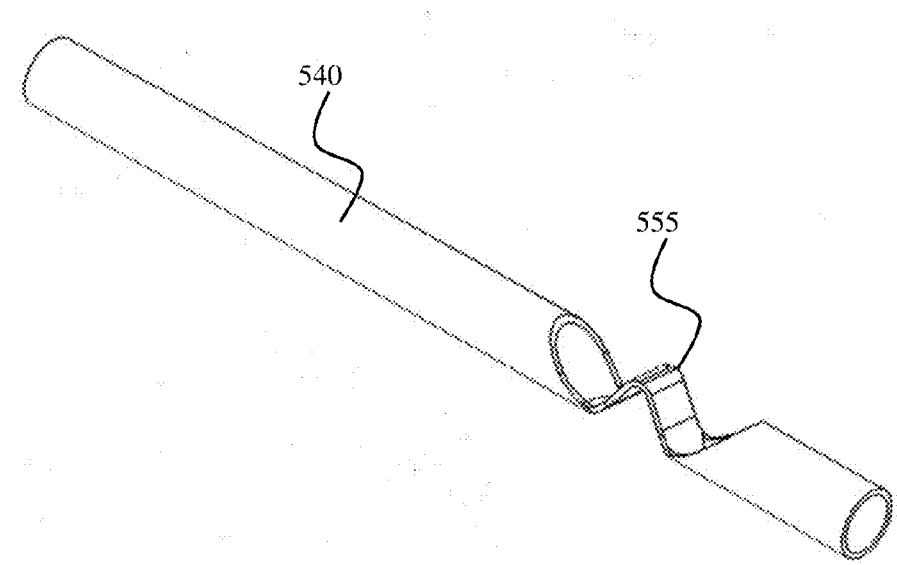
FIG. 5B is a perspective illustration of an alternative embodiment of an inner tube showing the collapsible section in a collapsed position.

FIG. 5A illustrates a needle assembly embodiment having a collapsible section 550 with a single projecting section 555 such as a collapsible leg. FIG. 5B illustrates how the projecting section 555 advances into the interior cavity of the inner tube 540 when collapsed.

Figure 6A:
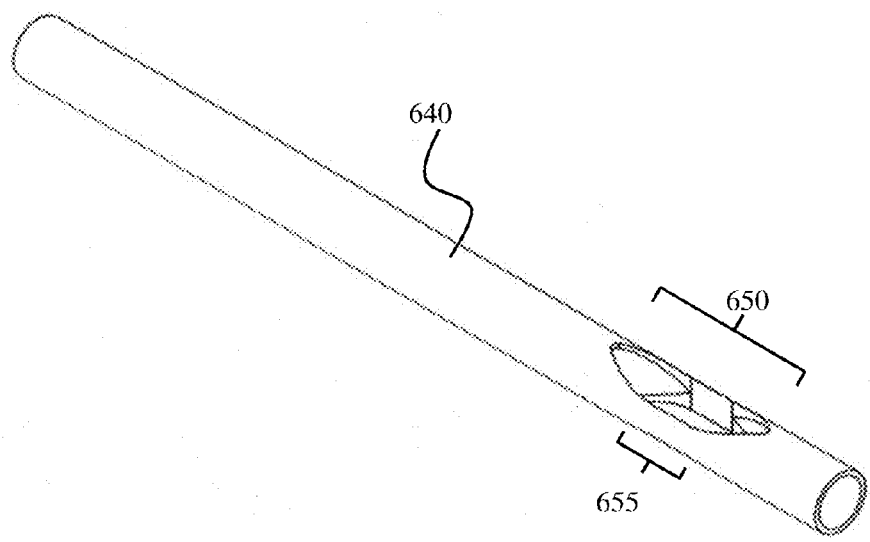
FIG. 6A is a perspective illustration of an alternative embodiment of an inner tube.
Figure 6B:
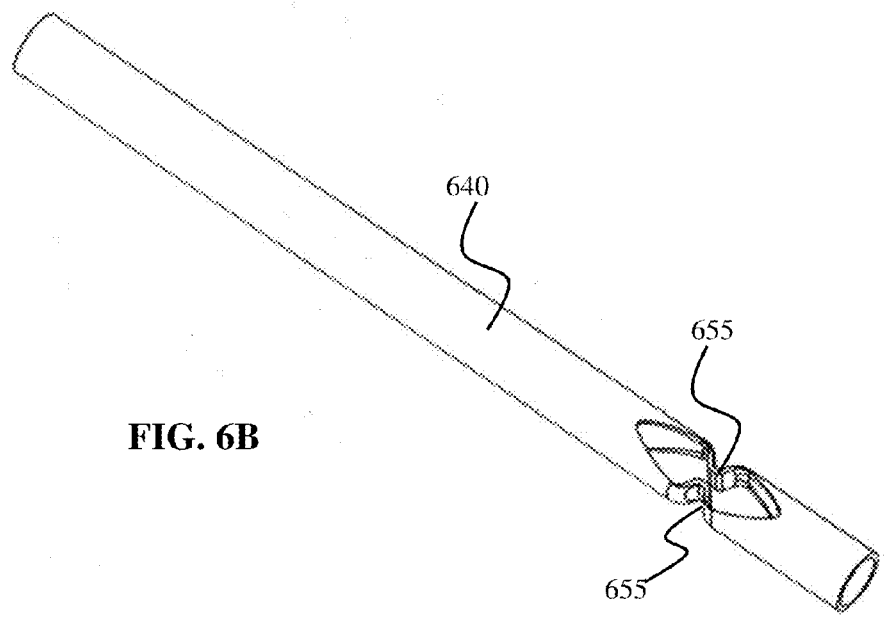
FIG. 6B is a perspective illustration of an alternative embodiment of an inner tube showing the collapsible section in a collapsed position.

FIG. 6A illustrates a needle assembly embodiment having a collapsible section 650 with two, generally symmetric projecting sections 655 on opposite sides of the walls of the inner tube 640. FIG. 6B illustrates how the projecting sections 655 advance into the interior cavity of the inner tube 640 when collapsed.

Figure 7A:
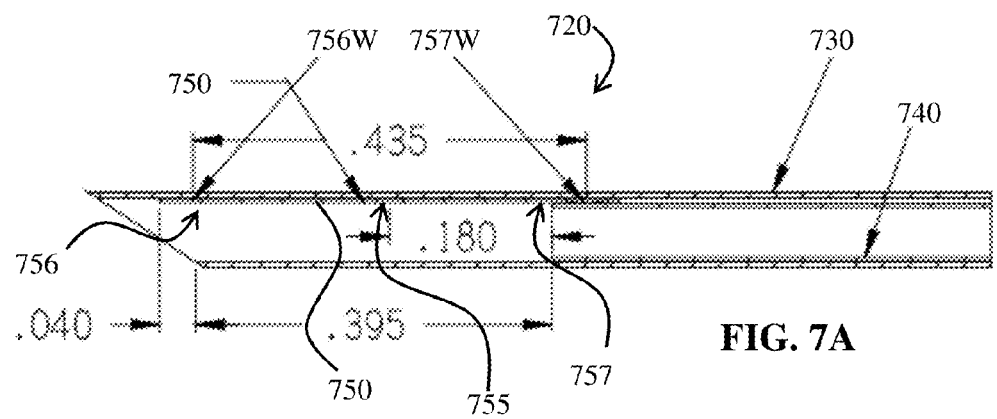
FIG. 7A is a side cut-away view of one embodiment of a needle assembly with the collapsible section in a neutral position.
Figure 7B:
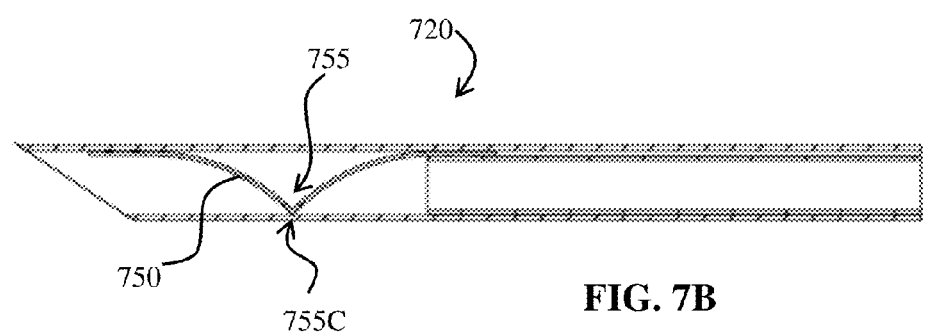
FIG. 7B is a side cut-away view of the embodiment of FIG. 7A with the collapsible section in a collapsed position.

FIGS. 7A and 7B illustrate example embodiments of a needle assembly 720. In this embodiment, the needle assembly 720 comprises an inner tube 740, an outer cannula 730 and a collapsible section 750. In this embodiment, the inner tube 740 may be used with an outer cannula 730 that may be a biopsy needle. The outer cannula 730, comprises a tube having a proximal/head portion and proximal/head end, a distal portion and distal end which may be sharpened, and an interior cavity dimensioned to receive the inner tube and collapsible section. The inner tube comprises an inner tube having an interior cavity, a distal portion and a proximal portion. The collapsible section 750 comprises a distal section 756, a proximal section 757 and a middle section 755 and the collapsible section is configured to deform to a collapsed position by a forward movement of the proximal section of the collapsible leg within an interior cavity of the biopsy needle. In this embodiment, the collapsible section is coupled to the distal portion of the inner tube 740 and the distal portion of the outer cannula 730. In this embodiment, the collapsible section 750 comprises a collapsible leg which may be an elastically collapsible leg.

The collapsible section 750 may be made from any material that allows the section to collapse or deform. In embodiments, the collapsible section 750 is made from elastic material such as, but not limited to super elastic materials as described above including elgiloy. One embodiment of elgiloy is a Co—Cr—Ni Alloy consisting of 39-41% Cobalt, 19-21% Chromium, 14-16% Nickel, 11.3-20.5% Iron, 6-8% Molybdenum, and 1.5-2.5% Manganese. Elgiloy is a beneficial material because some embodiments are corrosion resistant and exhibit high strength, ductility, and good fatigue life.

Figure 7C:
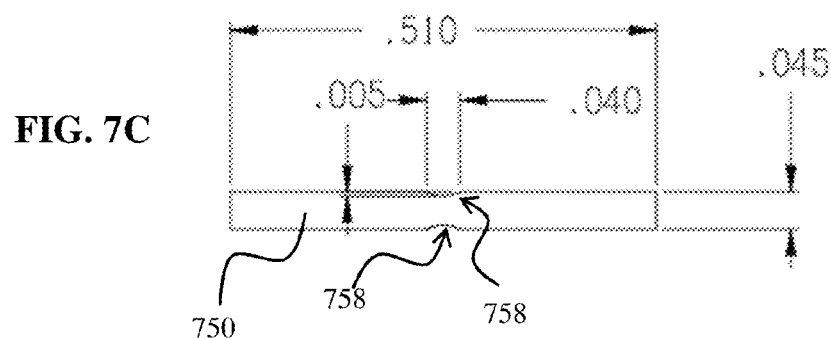
FIG. 7C is a top view of one embodiment of a collapsible section.
Figure 7D:
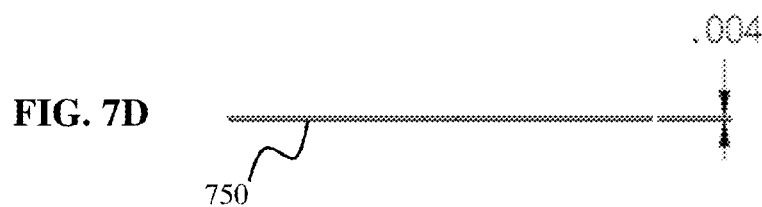
FIG. 7D is a side view of the embodiment of the collapsible section of FIG. 7C.

As illustrated here, and more particularly in FIGS. 7C and 7D, the collapsible section 750 may be a single leg shaped as a generally flat elongated strip. FIG. 7C illustrates a top view of one embodiment of the collapsible section 750 which may include a pair of notches 758 narrowing the width of the collapsible section 750 at any particular point. A flat elongated strip shape of the collapsible section 750 enables the section to be more easily collapsed and provides for a more firm engagement of the section with the outer cannula when engaging the tissue portion. The flat shape of leg may be more easily collapsed than a leg made from a cut out of a tube because the curve of the wall of the inner tube may provide more resistance to collapsing. The notches 758 or other manufacturing means such as cutting, etching or scoring may provide characteristics to further promote collapsing. Having a separate collapsible section 750 coupled to the inner tube 740 and the outer cannula 730 also allows the needle assembly 720 to be made from less expensive materials than would be required by having the collapsible section be integral to the other elements which may require the entire inner tube or outer cannula, or portions of them, to be manufactured from elastic or super elastic materials that may be more expensive and may require different manufacturing processes to create. Having the collapsible section 750 coupled, rather than integral to either of the tubes, also allows the collapsible section 750 to be welded or otherwise coupled to the inner tube and/or the outer cannula. In some embodiments, a welded coupling, shown here as weld 757W and weld 756W, to the tubes helps the collapsible section more easily maintain the beneficial properties of the generally flat shape.

In this embodiment, the collapsible section 750 is coupled to the exterior wall of the inner tube 740 with the weld 757W such that a forward movement of the inner tube urges the proximal section of the collapsible section 750 to move forward. The coupling may be provided by a direct attachment, connection, attachment with an intermediary element or it may be provided by other means such as being integral to the inner tube, having an intermediate element between the leg and inner tube or having the leg simply rest against the inner tube. Coupling may also be provided by any type of connection such as, but not limited to adhesives, welding, rivets or mating connections.

As shown in FIG. 7B, the coupling is such that when the distal section of the collapsible section 750 is constrained or otherwise restricted to move less than its proximal section, a projecting section, here the middle section 755 of the collapsible section 750, is urged into and across a portion of the interior cavity of the inner tube 740 or the outer cannula 730 interior cavity so that the collapsible section 750 can engage a portion of the tissue portion inserted through the proximal end of the inner tube 740 and/or outer tube needle 730 and into the tubes interior. As described above, the middle section 755 is a projecting section that projects into the inner cavity of the outer cannula and/or the inner tube and positions the projecting section across a portion of the interior cavity of the outer cannula and proximal to a portion of the interior cavity wall of the outer cannula. As shown, the projecting section, here the middle section 755 of the collapsible section 750 may be configured to further comprise a cutting edge 755C to engage or otherwise assist in the retaining of the tissue portion in the needle assembly.

In the embodiment shown in FIGS. 7A and 7B, the collapsible section 750 may also be coupled to a portion of the outer cannula 730. In this embodiment, the distal section 756 of the collapsible section 750 is coupled to the distal portion of the outer cannula 730 by a weld 756W. This coupling provides the restriction of the collapsible leg's distal section so that when the inner tube and the proximal section of the collapsible section 750 is urged forward but the distal section of the collapsible section 750 is restricted, the middle section 755, or projecting section, is urged into the interior of the outer cannula 730. With this embodiment, when a tissue portion is received into the interior of the inner tube 740 and the outer cannula 730, the projecting section 755 frictionally engages the tissue portion by a force against the interior cavity walls of the inner tube 740 or outer cannula 730. The engagement may sever the tissue portion or the engagement may be maintained such that when a retrograde force is applied to the needle assembly 720, the projection section 755 retains the tissue in the interior of the inner tube 740 and sheers or otherwise cuts the tissue portion from the rest of the tissue.

Also shown in FIG. 7A are example dimensions of one embodiment of the needle assembly 720 elements for illustration purposes only and are not for limitation. The dimensions may be any suitable dimensions to provide the features described herein and are expected to be varied based on the application of the needle assembly. In the example shown, the collapsible section 750 is about 0.510 inches (12.954 mm) long, a distance between the coupling (775W and 756W) of the collapsible section 750 to the outer cannula 730 and the inner tube 740 is about 0.435 inches (11.049 mm), a gap between the distal end of the inner tube 740 and a middle section 755 of the collapsible section 750 is about 0.18 inches (4.572 mm), a distance from a distal edge of the collapsible section 750 and a distal edge of an opening of the distal end of the outer cannula is about 0.04 inches (1.016 mm) and a distance from the distal edge of the opening of the outer cannula 730 to the distal end of the inner tube 740 is about 0.395 inches (10.033 mm).

Referring to FIG. 7C, showing a top view of one embodiment of the collapsible section and illustrating, for example only, example dimensions of the collapsible section 750 the length may be about 0.510 inches (12.954 mm), a width may be about 0.045 inches (1.143 mm), a length of the notch may be about 0.040 inches (1.016 mm) and a depth of the notch may be about 0.005 inches (0.127 mm). As shown in the side view of FIG. 7D, a thickness of the collapsible section 750 may be about 0.004 inches (0.102 mm).

Although the embodiment illustrated in FIGS. 7A and 7B described above has the collapsible section 750 coupled to the inner tube 740 and outer cannula 730, other embodiments are anticipated that provide the same functions. For example, and not for limitation, it is anticipated that the inner tube may comprise multiple inner tube sections that are coupled by the collapsible section; the collapsible section may be integrated into a portion of the inner tube; or the collapsible section may contain a portion, such as a tubular portion, at its distal end that engages a portion of the outer cannula and restricts movement of the collapsible section while a proximal section engages the inner tube to receive the forward force. It is also anticipated that the collapsible section may be welded to the interior wall of the inner tube.

Although the above example embodiments describe the projecting section of the collapsible section being the middle section, it is also contemplated that the projecting section may be positioned in other sections of the collapsible section. For example, the projecting section may be placed closer to the distal section of the collapsible section. Configuring the projecting section in difference places on the collapsible section may be done by placing notches, etchings or other similar characteristics in particular sections to promote the collapsing of the collapsible section at a particular location.

Figure 8A:
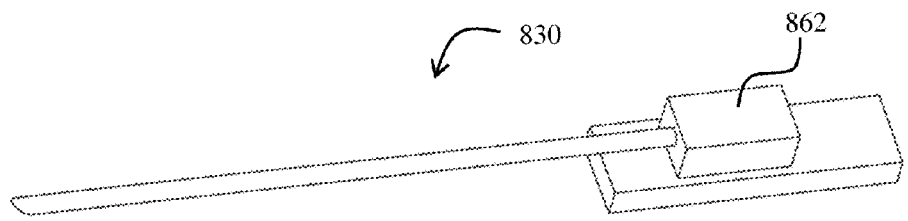
FIG. 8A is a top perspective view of one embodiment of an outer cannula and a slide.
Figure 8B:
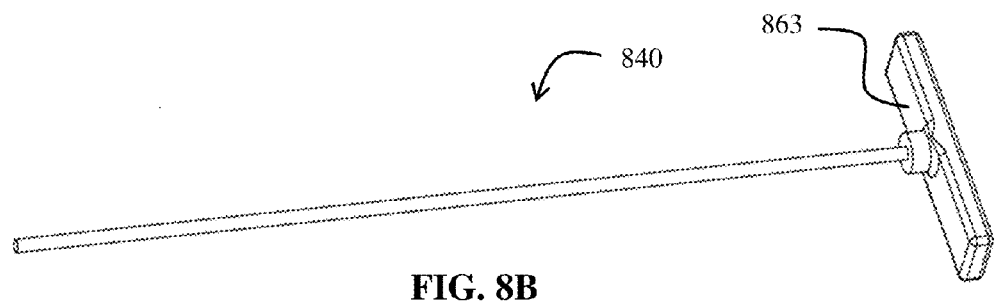
FIG. 8B is a top perspective view of one embodiment of an inner tube and an inner tube handle.
Figure 8C:
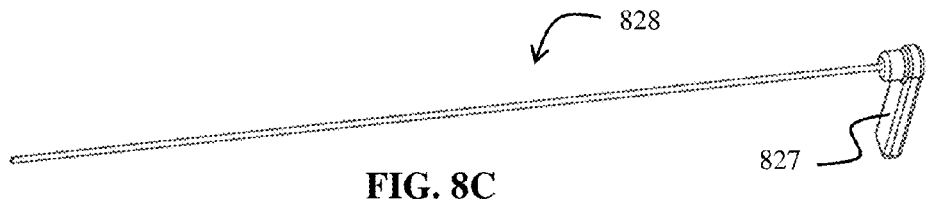
FIG. 8C is a top perspective view of one embodiment of a plunger and a plunger handle.

FIGS. 8A-8D illustrate an example embodiment of the needle assembly of FIGS. 7A and 7B further comprising a plunger. FIG. 8A illustrates an embodiment of the outer cannula 830 with a cam 862 coupled to its proximal portion or proximal end. The cam 863 may be configured to receive the restraining for and transfer it to the outer cannula. FIG. 8B illustrates an embodiment of the inner tube 840 with an inner tube cam 863, here a handle, on a proximal portion or proximal end. The inner tube may be coupled to the inner tube cam to receive the forward force and transfer that to the inner tube 840. FIG. 8C illustrates an embodiment of the plunger 828 with a plunger handle 827.

Figure 8D:
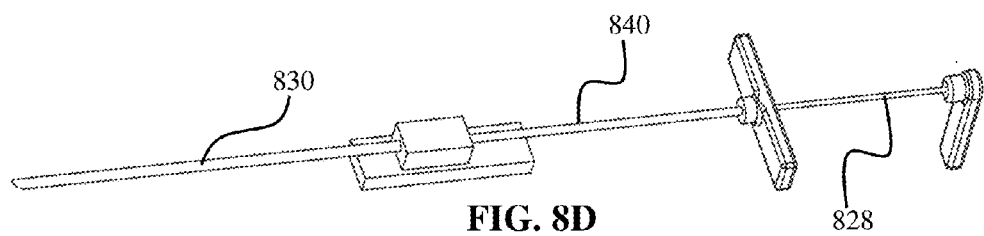
FIG. 8D is a top perspective view of one embodiment of a needle assembly with the plunger received in an inner tube and the inner tube received in the outer cannula.

As shown in FIG. 8D, the plunger 828 is slidably received in the inner tube 840. Both the inner tube 840 and the plunger 828 may then be received in the outer cannula 830. The plunger 828 is dimensioned to be able to extend through a majority of the inner tube 840 so that it may expel or otherwise push out any tissue or tissue portion that may be in the inner tube 840. The inner tube 840 is dimensioned to extend through the outer cannula 830 to a point where the collapsible section (not shown) can collapse and engage the tissue. The outer cannula 830 is dimensioned to penetrate the tissue and interoperate with other assembly elements such as any triggers, cams, handles or a holder assembly.

It has been found that in some embodiments of the needle assembly, some tissue is able to migrate behind the collapsible section and eventually impact the needle assembly's efficient capturing of the tissue portion. Non-sample portion material and other residue of the tissue portion may separate from the sample portion of the tissue as a non-sample portion material and this non-sample tissue migrates around the collapsible section when it is in the collapsed position so that is becomes positioned in a space between the underside of the collapsible section and the inner wall of the outer cannula and interferes with a complete return of the collapsible section to the uncollapsed or neutral position. This situation may prevent efficient use of the needle assembly when trying to remove the tissue portion. This situation may also prevent efficient use of the needle assembly when the needle assembly is reused to obtain multiple tissue portions as a result of multiple instances of non-sample portion material becoming positioned between the collapsible section and the outer cannula. In some embodiments of the needle assembly, an aperture or other opening may be provided at this point in the outer cannula that allows non-sample portion material and other matter to pass through and be expelled from the space, like a pocket, under the collapsible section when it is in or tries to move into the uncollapsed or neutral position. The aperture may comprise an opening, defined by opening walls in the outer cannula, extending through the interior cavity wall from an interior cavity wall inner surface to an exterior surface of the interior cavity wall. The aperture may also comprise any means to pass tissue from under the collapsible section and the interior cavity of the needle assembly.

FIGS. 12A-12H illustrate one example embodiment of the needle assembly. FIGS. 12A-12E show embodiments with the collapsible section in a collapsed position and FIGS. 12F-12H show embodiments with the collapsible section in a uncollapsed or neutral position. Consistent with example embodiments described herein, these embodiments include a needle assembly generally comprising an inner tube, an outer cannula and a collapsible section.

FIG. 12A shows a bottom cut-away view of one embodiment of the needle assembly 1220 having an aperture in the outer cannula. In this embodiment, consistent with the embodiments described herein, the inner tube may be used with the outer cannula. The outer cannula, generally comprises a tube having a proximal/head portion and proximal/head end, a distal portion and distal end which may be sharpened, and an interior cavity dimensioned to receive the inner tube and collapsible section. In this embodiment, as FIG. 12E shows for the distal section 1220C (see also FIG. 12B showing detail C of FIG. 12A) of needle assembly 1220, the outer cannula 1230 may also have an aperture 1237 positioned opposite the "pinch point" or protruding section of the collapsible section 1250 when the needle assembly 1220 is configured for operation. The aperture 1237 is positioned and sized to allow tissue that may fall under or behind the collapsible section 1250 so that the tissue may pass and be expelled out of the outer cannula 1230 and out of the needle assembly 1220. The aperture 1237 may be defined by any type of opening through the inner cavity walls of the outer cannula 1230 allowing tissue to pass and be expelled from under the collapsible section 1250. The shape of the aperture may be any shape for example and not for limitation, the shape may be a rectangle, an oval or a rectangle with rounded or otherwise curved edges. In some embodiments, to prevent the collapsible section 1250 from extending outside of the aperture, the shape of the aperture may have a width less than the width of the collapsible section and in some embodiments the length of the aperture may be less than the length of the collapsible section 1250. For example and not for limitation, FIG. 12E shows a portion of the outer cannula 1230 partially cut away with aperture 1237 extending from the interior cavity wall inner surface of the outer cannula to an exterior surface of the interior cavity wall of the outer cannula. Although the aperture 1237 will allow tissue to pass and be expelled from the outer cannula 1230 (a non-sample portion of the tissue), the needle assembly 1220 is configured to still retain a tissue portion as a sample portion of the tissue in the interior cavity of the needle assembly 1220 to be expelled later as a tissue sample.

FIG. 12B shows details of detail C of FIG. 12A. As can be seen in FIG. 12B, the distal end 1220C of the needle assembly shows the outer cannula 1230, the aperture 1237 and the underside of the collapsible section 1250 of the inner tube.

FIG. 12C shows a side cut-away view of the embodiment of the needle assembly 1220 with the collapsible section in a collapsed position.

FIG. 12D shows a closer view of the needle assembly 1220 of FIG. 12C where the outer cannula 1230, the inner tube 1240 and the collapsible section 1250 can be seen in a collapsed position. Also show are optional features such as a weld 1238 of the distal portion of the collapsible section 1250 to the outer cannula 1230 as well as a weld 1239 of the proximal potion of the collapsible section 1250 to a distal portion of the inner tube 1240.

FIG. 12E shows a bottom perspective view of the distal portion 1220C of the needle assembly 1220 showing an example embodiment of the outer cannula 1230 with the aperture 1237 and showing how the aperture 1237 is positioned below the collapsible section 1250 as the collapsible section 1250 is in some degree of collapse.

FIGS. 12F-12H show the example embodiments of FIGS. 12A-12E with the collapsible section in an uncollapsed or neutral position. FIG. 12F shows a side cut-away view of needle assembly 1220. FIG. 12G shows a bottom cut-away view with detail D showing the outer cannula 1230 and the aperture 1237 positioned at its distal end. FIG. 12H shows a side cut-away view of the distal end 1220D of the needle assembly showing the collapsible section 1250 in an uncollapsed or neutral position.

Although FIGS. 12A-12F show a single aperture in the outer cannula 1230, it is understood that in some embodiments that may have multiple locations where tissue may migrate between the collapsible section and the outer cannula, more than one aperture may be provided. For example, embodiment of the needle assembly having multiple collapsible sections may have multiple apertures with apertures positioned to allow the passing of tissue from under each collapsible section.

Figure 13A:
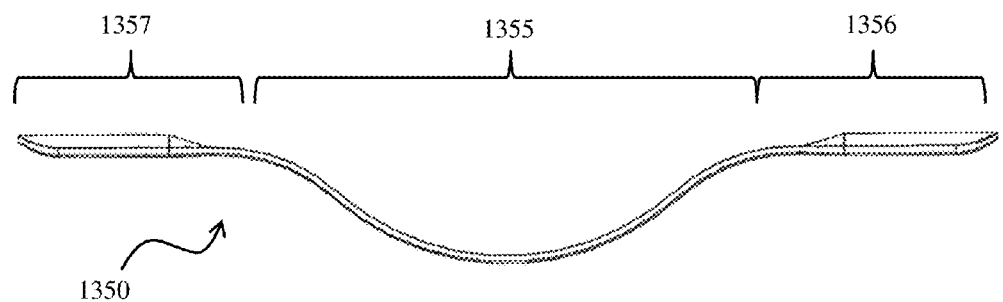
FIGS. 13A-13C show different views of an example embodiment of a collapsible section of a needle assembly.
Figure 13B:
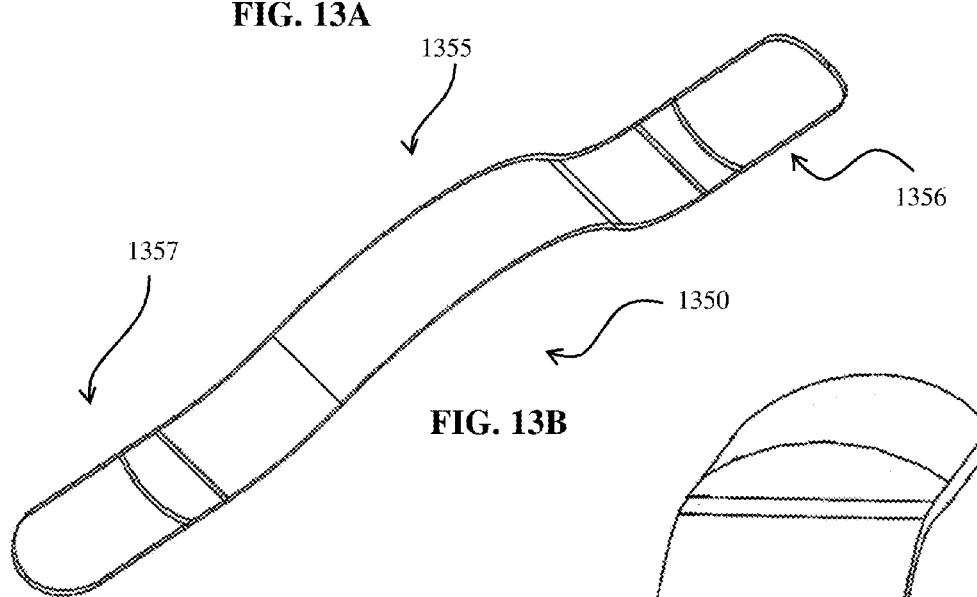
Figure 13C:
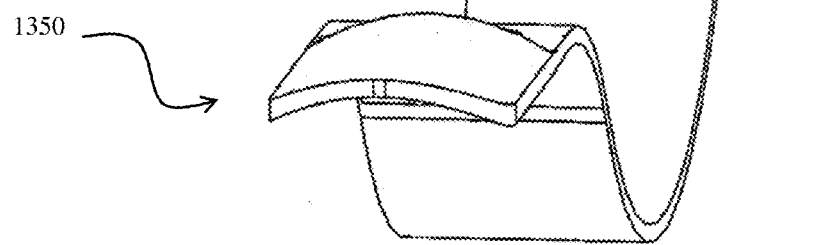

FIGS. 13A-13C show example embodiments of the collapsible section 1350 that may be used with the needle assemblies described herein. These example embodiments may be coupled with the inner tube and/or the outer cannula to provide the same collapsing, cutting or pinching features as described above. The material that may be used for these embodiments may be the same materials as are used for the inner tube or the outer cannula. In some embodiments, the collapsible section 1350 is a separately manufactured element and the material used is different than that of the inner tube and the outer cannula. For some embodiments, if the collapsing properties of the collapsible section 1350 benefit from material that is more expensive than is needed for the inner tube or outer cannula, having a different material for the collapsing section may reduce the overall cost of material and the assembly. For example, the collapsible section 1350 may be made from a stainless steel, an elgiloy or a super elastic material and this section may be welded, glued or otherwise coupled to the inner tube and/or the outer cannula that are made from less expensive materials.

As shown in FIG. 13A, the collapsible section 1350 may have a distal section 1356, a proximal section 1357 and a middle section 1355 and the collapsible section 1350 is configured to deform to a collapsed position by a forward movement of the proximal section 1357 of the collapsible leg within an interior cavity of the outer cannula. In an example embodiment, the collapsible section 1350 is coupled to the distal portion of the inner tube and the distal portion of the outer cannula. In some embodiments, the collapsible section 1350 comprises an elastically collapsible leg. As shown, the shape of the projecting section, here the middle section 1355, of the collapsible section 1350 may be rounded or curved and still provide enough force to engage the tissue and keep a tissue portion in the needle assembly when removed from the tissue. Also shown are curved ends for the distal and proximal sections of the collapsible section 1350. The curved shaped of these ends along its width allow for more surface contact and better coupling to the surfaces of the inner tube and the outer cannula when the collapsible section 1350 is coupled to these elements and these elements also have curved surfaces.

Figure 14A:
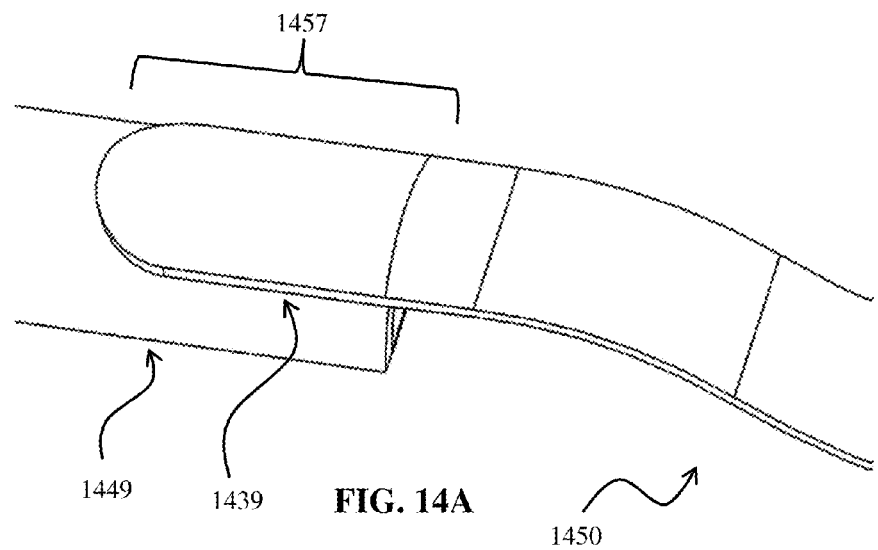
FIGS. 14A-14B show perspective views of portions of an example embodiment of a needle assembly.
Figure 14B:
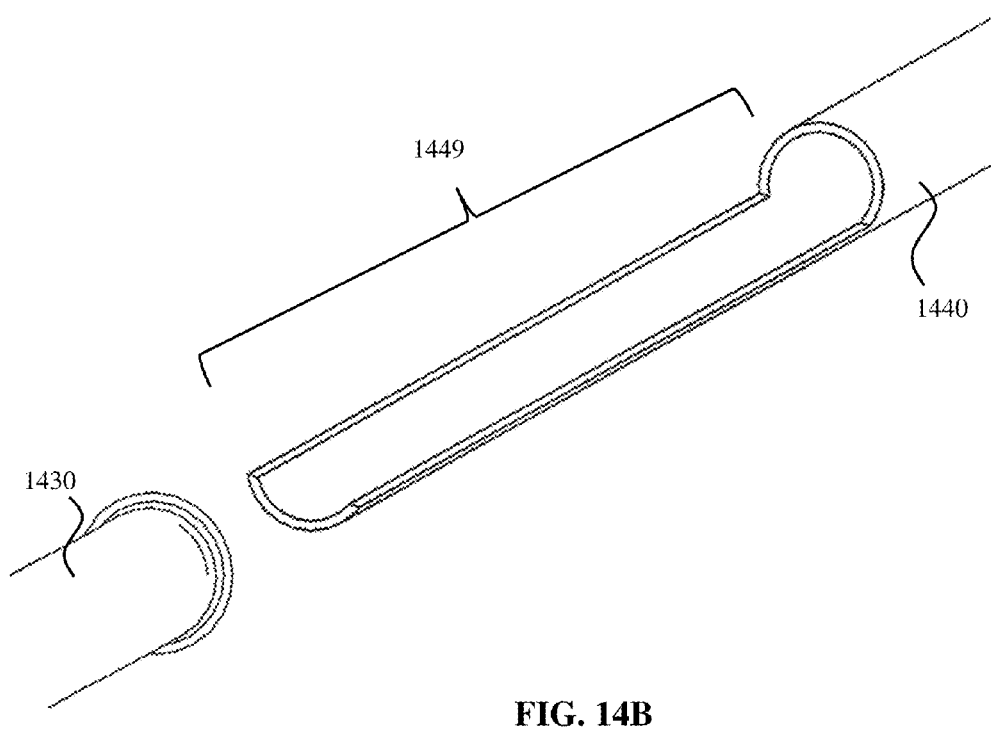

As shown in the example embodiments of FIGS. 14A-14C, the inner tube comprises an inner tube 1440 having an interior cavity, a distal portion 1449 and a proximal portion. In this embodiment, the distal portion 1449 is defined as a portion of the distal end of the inner tube 1440 with a portion of the inner tube cut-away. In some embodiments, the cut-away portion allows a larger diameter tissue portion size to be retained within the outer cannula 1430 by holding the tissue portion between the distal portion 1449 and the interior wall of the outer cannula. In some embodiments the length of the cut-away portion is longer than the planned length of the tissue portion to be removed from the tissue to allow the tissue portion to be held within this cut-away portion. In the example embodiments of FIGS. 14A-14C, the proximal section 1457 of the collapsible section 1450 is coupled to the distal portion 1449 of the inner tube 1440 at weld 1439 (see FIG. 14A) and the distal portion of the outer cannula 1430 (not shown). In some embodiments, the coupling is done by welding the collapsible section 1450 to the distal portion of the inner tube 1440 (at weld 1439) and the outer cannula 1430 (weld not shown). As shown, in some embodiments the collapsible section 1450 is welded to the outer surface of the inner tube 1440 and the inner surface of the outer cannula 1430.

Although the cut-away portion of the distal portion 1449 is shown as being about one third of the normal circumference of the inner tube (with about two thirds cut-away), it is understood that the cut-away portion of the distal portion 1449 may be any portion of the inner tube and the distal portion 1449 may not include any cut-away portion at all. The distal portion 1449 may also comprise other elements to couple the distal end of the inner tube 1440 to the collapsible section 1450.

Although the embodiments of FIGS. 12A-14C describe elements of one example embodiment the needle assembly having an aperture, it is understood that other embodiments of the needle assembly may further include the aperture as described herein. For example and not for limitation, the embodiments of FIGS. 2A-2D, 3A-3C and 7A-7D may also include one or more aperture in the outer cannula. Additionally, other embodiments of the needle assembly may comprise the collapsible section and distal end configurations illustrated by FIGS. 12A-14C.

Figure 9A:
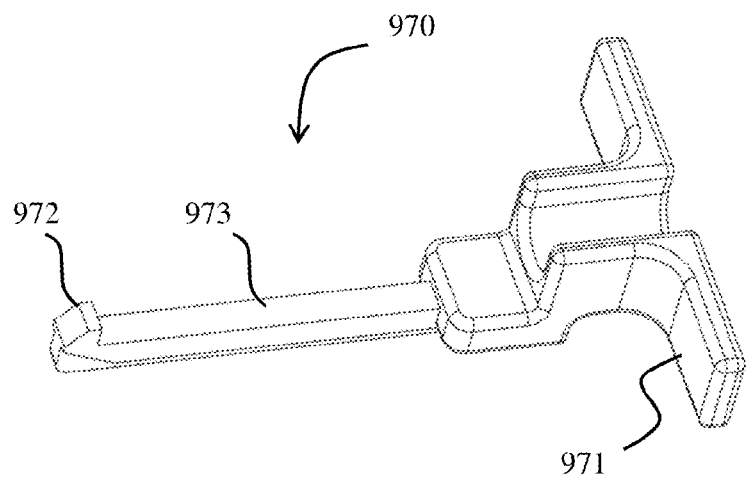
FIG. 9A is a top perspective view of one embodiment of a latch.
Figure 9B:
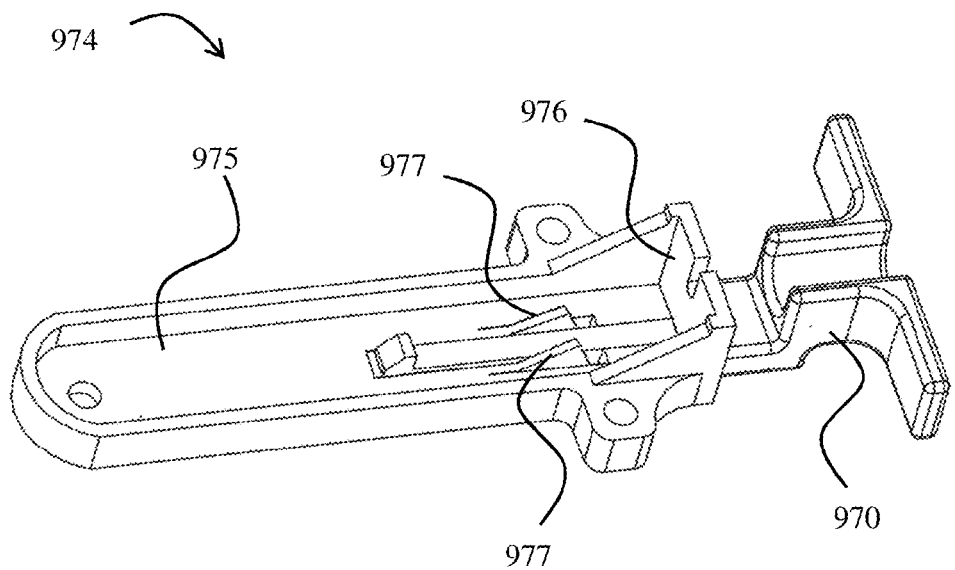
FIG. 9B is a top perspective view of one embodiment of a latch received in the slide guide.

FIGS. 9A and 9B illustrate other elements as part of one embodiment of a needle assembly. FIG. 9A illustrates one embodiment of a latch 970 comprising a latch key 972, a latch extension 973 and a latch handle 971. FIG. 9B illustrates one embodiment of a slide guide 974 to slidably receive the latch 970 and the outer cannula cam (now shown). The slide guide 974 comprises a slide channel 975, a slide stop 976 and one or more guide keys 977. The slide guide 974 and the guide keys 977 are configured to engage the underside of the slide when the slide is pulled towards the slide stop 976. The guide keys 977 are also able to move in and out of the slide guide 974 by a guide key ramp (not shown) that is moved or deflected out of the slide guide 974 by the forward movement of the latch key 972 over the guide key ramp. As illustrated, the guide keys 977 and the guide key ramp are a cut out portion of the slide guide 975 so that they can be used to hold the slide in the ready configuration and deflect to release the slide and outer cannula by forward movement of the latch key 972 so that they can advance forward.

Figure 10A:
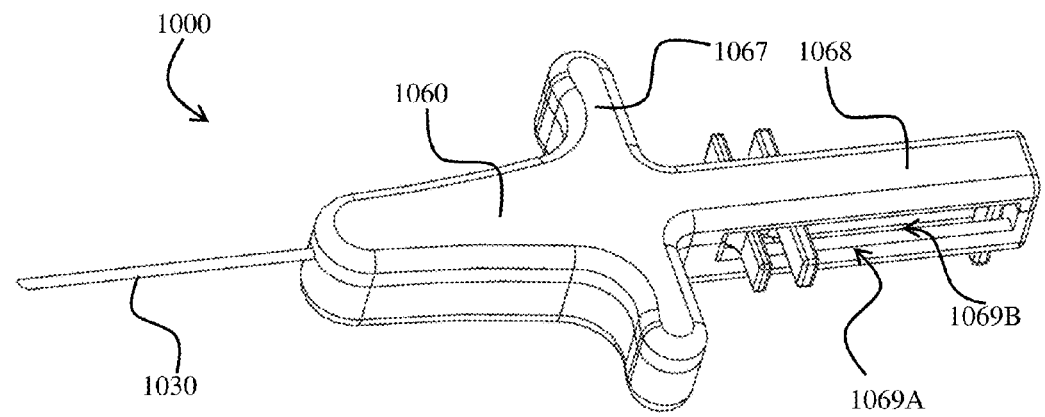
FIG. 10A is a top perspective view of one embodiment of a tissue removal apparatus.

FIG. 10A illustrates one embodiment of tissue removal apparatus 1000. This example embodiment of the tissue removal apparatus 1000 includes a holder assembly 1060 and a needle assembly with the outer cannula 1030 shown.

Figure 10B:
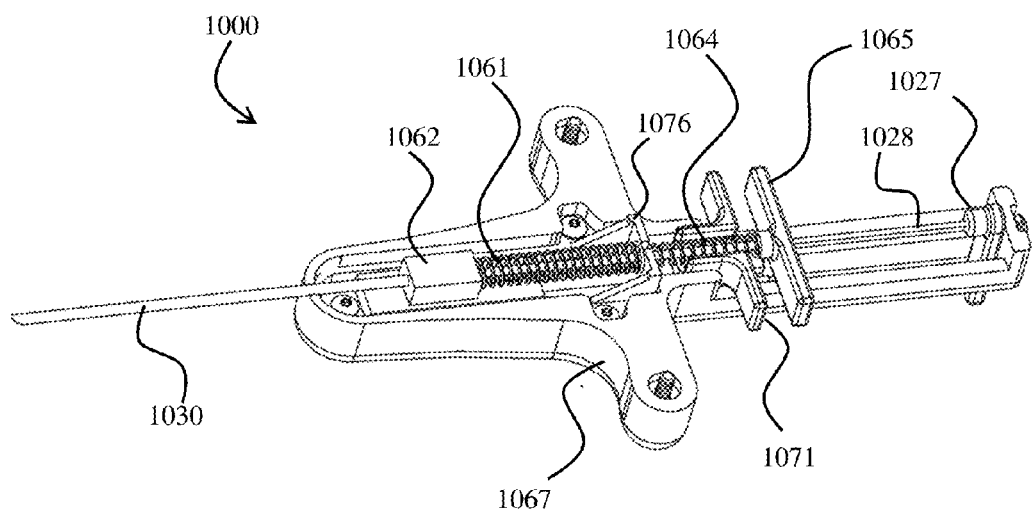
FIG. 10B is a top perspective view of one embodiment of a tissue removal apparatus with the top removed.

FIG. 10B illustrates a view of the tissue removal apparatus 1000 of FIG. 10A without the top. In this embodiment, the needle assembly is similar to the embodiments of FIGS. 8A and 8B with the inner tube, the outer cannula 1030 and the collapsible section. The inner tube (received in outer cannula) has an inner tube handle 1065 as a cam and the outer cannula 1030 has an outer cannula slide 1062 as a cam. This embodiment also has a plunger 1028 with a plunger handle 1027. Also shown is an example embodiment of a trigger mechanism and a cocking mechanism. In this embodiment, the trigger mechanism comprises the guide, the latch, the latch handle 1071, latch key, the guide keys, the guide key ramp and force elements that operationally engage the inner tube cam and the outer cannula slide 1062 to change the collapsible section to its collapsed position. The trigger mechanism may be configured to automatically provide the forward force to the inner tube or inner tube cam 1065. This trigger mechanism may also provide a forward force to advance the outer cannula 1030 into the tissue. As shown, a first force element 1061, here a spring, rests against and engages the outer cannula slide 1062. The outer cannula slide 1062 is coupled to the outer cannula 1030 so that it functions as a cam to move the outer cannula 1030. The first force element 1061 is constrained between the slide stop 1076 of the slide guide and the slide 1062 so that it provides a forward force on the slide 1062 and outer cannula 1030. The slide 1062 is retained in a position by the guide keys of the guide engaging the underside of the slide 1062 such that it compresses the first force element 1061. When the latch key is moved forward by the latch handle 1071, such as applying a forward force, it pushed the latch key against the guide key ramp, deflecting the guide keys out of the guide and out of engagement with the underside of the slide 1062, such that it releases the slide 1062 and the first force element 1061 which then advances the slide 1062 and the outer cannula 1030 within the slide guide. The slide 1062 and the outer cannula 1030 advance to a position until the slide 1062 can no longer move within the guide. The slide 1062 and the outer cannula 1030 may be kept in that advanced position by the force of the first force element 1061 or by other mechanical means. Through this advancing of the outer cannula 1030, in some embodiments, the latch and the inner tube is also advanced. This is because in those embodiments, the inner tube 1040 is coupled to the outer cannula 1030 by the collapsible section (not shown) and the latch is engaged with the slide 1062.

The holder assembly 1060 may be configured to provide a forward force on the inner tube and a restraining force on the outer cannula 1030 whereby when the collapsible section is coupled to the inner tube and the outer cannula 1030, the forward force on the inner tube and the proximal section of the collapsible section and the restraining force on the outer cannula 1030 causes a restrained movement of the distal section of the collapsible section relative to the proximal section of the collapsible section and may collapse the collapsible section into a collapsed position. The restrained movement may also be a lack of movement. In the embodiment of FIG. 10B, when the inner tube and the outer cannula 1030 are in the advanced position, the inner tube may be further advanced by providing a forward force to advance the inner tube. The forward force may be a manual or spring force on the inner tube cam, here the inner tube handle 1065. The forward force may also be provided by the momentum of the inner tube and inner tube handle 1065 as they move forward with the outer cannula 1030. When outer cannula 1030 is restrained by the slide 1062 and the slide guide, the restraining force is applied to the outer cannula 1030. Together, the forward and restraining forces collapse the collapsible section into the collapsed position and the collapsible section engages the tissue portion within the needle assembly so that when the needle assembly is withdrawn from the tissue, the tissue portion is withdrawn in the needle assembly. In the embodiment of FIG. 10B, the inner tube handle 1065 functions as the inner tube cam and spring 1064 functions as a buffer spring to counter some of the momentum of the inner tube and inner tube cam as they move forward with the outer cannula 1030.

In this example embodiment, the plunger 1028 may be used to expel the tissue portion from the needle assembly. As shown, the plunger 1028 may be configured so that advancing it by putting a forward force on the plunger handle 1027 causes the plunger 1028 to advance and extend through the inner tube and push the tissue portion out of the distal end of the inner tube and outer cannula 1030.

Although this illustrated embodiment has a trigger mechanism to provide the forward forces on needle assembly elements, it is understood that the elements may also be trigged by manual forces. For example, the outer cannula may be positioned in the tissue by manually manipulating the holder assembly and outer cannula. Also, the inner tube and collapsible section may be triggered by manually providing a forward force on the inner tube or the inner tube cam and advancing it relative to the outer tube which may be restrained mechanically or manually.

FIG. 10B also illustrates an embodiment of a cocking mechanism to allow for reuse of the tissue removal apparatus 1000 and the needle assembly. The cocking mechanism may comprise the interoperation of elements such as the latch handle 1071, the outer cannula 1030, the inner tube (received in the outer cannula), the slide 1062 and the latch key. In this embodiment, the cockling mechanism is configured such that when the apparatus is in the advanced position as shown, pulling the latch handle 1071 will put a retrograde force on the inner tube and the outer cannula 1030. The retrograde force pulls the needle assembly back until the slide 1062 is engaged with the guide key. The guide key again retains the inner tube, the collapsible section and the outer cannula 1030 in the ready configuration for reuse.

Also shown in FIG. 10A are a holder assembly 1060, holder grips 1067, a channel tower 1068 and channels for the inner tube handle, the latch handle 1069A and a separate channel for the plunger handle 1069B.

Some embodiments of the inner tube comprise the inner tube having a body portion separated from a fore portion of the inner tube and the elastically collapsible leg is coupled to both the fore portion and the body portion of the inner tube. In this embodiment, the collapsible leg may be coupled to the fore portion of the inner tube by a first weld and the collapsible leg may be coupled to the body portion by a second weld.

Some embodiments of the needle assembly comprise at least one additional collapsible section such as an additional collapsible leg.

In some embodiments, the inner tube and the outer cannula/tube may have shapes that are not circular tubes. For example and not for limitation, the inner and outer tubes may have square, rectangular, triangular or oval shaped cross-sections.

Some embodiments of the collapsible section are also envisioned which include any mechanism to collapse a projecting section into the inner tube interior.

One Embodiment of the Tissue Removal Apparatus in Operation:

One example embodiment of methods of tissue removal are illustrated by the operation of one embodiment of the tissue removal apparatus which generally comprises the steps of positioning a needle assembly in a tissue, engaging a tissue portion and withdrawing the tissue portion from the tissue. For purposes of illustrating in more detail the operation of one embodiment of a tissue removal apparatus, and not for limitation, the operation of an apparatus for tissue biopsy is summarized in FIG. 11. This illustration is consistent with tissue removal apparatus of FIGS. 1, 2A-2D and 4.

Figure 11:
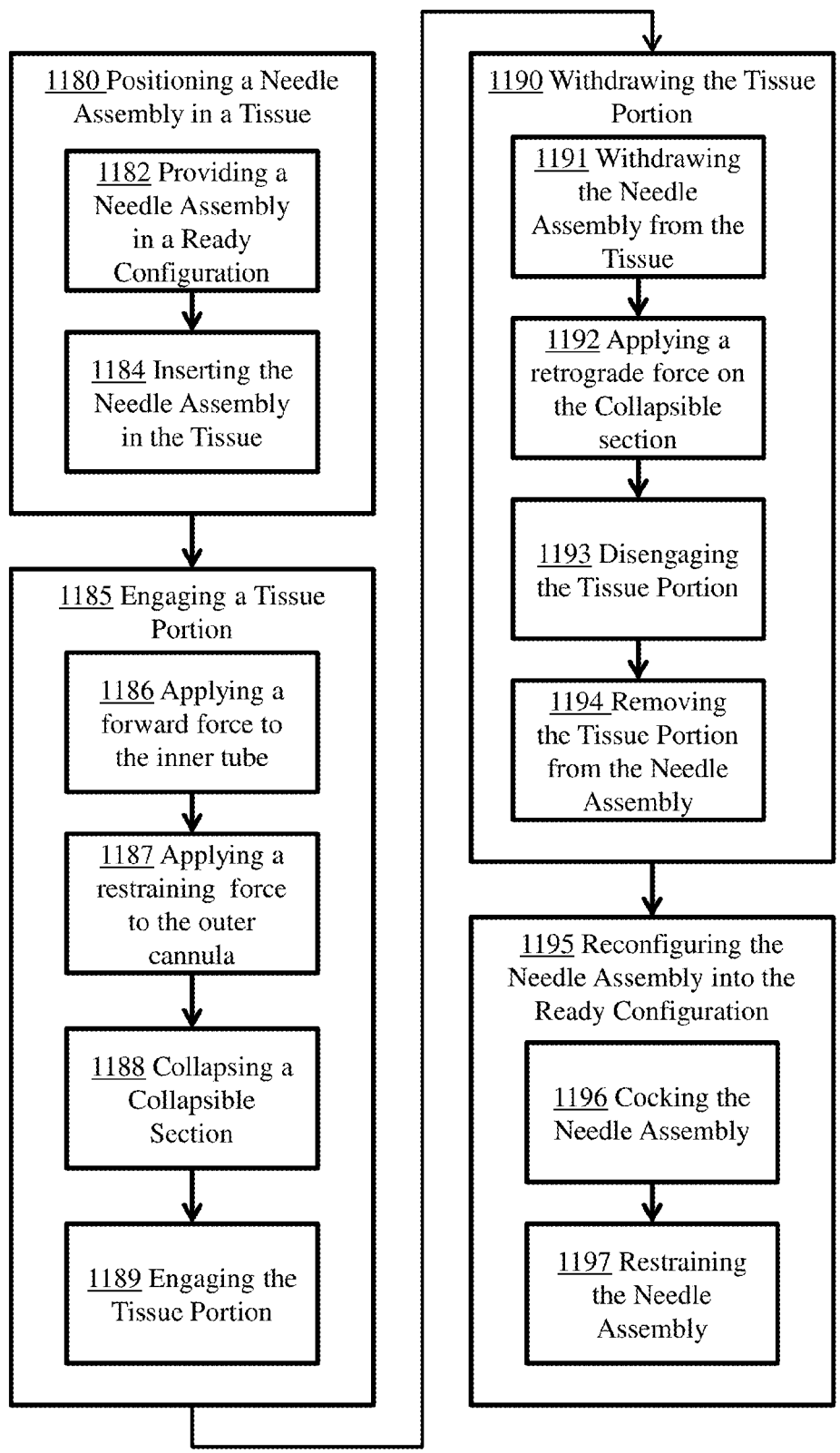
FIG. 11 is a process diagram illustrating the steps for one embodiment of methods for tissue removal.

Referring to FIG. 11, the steps for this embodiment of the methods generally comprise the step of positioning the needle assembly in the tissue at 1180, engaging a tissue portion of the tissue at step 1185, withdrawing the tissue portion at 1190 and may include reconfiguring the needle assembly in the ready configuration at step 1195.

The additional steps shown in FIG. 11 are illustrated referring to the example embodiments of the tissue removal apparatus of FIGS. 1, 2A-2D and 4. The apparatus for this example is initially provided in the ready configuration which puts the needle assembly in a ready position similar to those embodiments shown in FIGS. 2A-2D and 4. Referring to FIGS. 2A-2D, in a ready configuration, the needle assembly 220 is typically configured so that the trocar needle 228 is slidably positioned through both the inner tube 240 and the outer cannula 230 with the trocar needle sharpened distal end 229 protruding through the open distal end 234 of the outer cannula 230. In this embodiment, the trocar needle distal end 229 is sharp and pointed protruding slightly to form a needle-like tip in combination with the sharp serrated distal end of the distal portion 234 of the outer cannula 230. In the ready configuration, the collapsible section 250 is set in the neutral position so that it will actuate and change to a collapsed position when the triggering mechanism is triggered.

With this configuration, the process of operation starts with the step of positioning the distal end of the needle assembly 220. The needle assembly 220 is positioned, using a holder assembly as a handle, through and into the tissue by the user to a point for removing a section of the tissue. In one embodiment, the needle assembly 220 is positioned so that when the outer cannula 230 and inner tube 240 are advanced by triggering the trigger mechanism, they will advance into and retain the tissue portion desired to be removed.

With the needle assembly 220 positioned, the tissue portion of the tissue is then engaged. In one general embodiment, the step of engaging a tissue portion comprises applying a forward force to the inner tube 240, applying a retrograde force to the outer cannula 230 and collapsing the collapsible section 250 whereby the collapsible section 250 engages the tissue portion in the inner tube 240.

Referring to FIG. 4, in one embodiment, the step of engaging a tissue starts with a holder assembly 460 having a trigger mechanism. In this embodiment, the trigger mechanism comprises a trigger button 469, a latch 470 and force elements within the holder assembly 460. In this embodiment, the trigger button 469 is configured such that when it is pushed or depressed, it operationally engages a latch 470 which releases a force element 461 and the outer cannula 430 and inner tube (received in the outer cannula) are advanced into and around the tissue to be removed. In this embodiment, the outer cannula 430 is released by the latch 470 and advanced by a first force element 461 comprising a first spring operationally engaging and applying a first force to a first cam 462. In this embodiment, the trocar needle 428 is stationary in the holder assembly 460 and does not advance which lets the outer cannula 430 and inner tube advance with an empty interior portion. With this advance, the tissue portion is brought into the empty interior cavity of the inner tube. As the needle assembly 420 reaches its advancing limit, as defined by a positive stop, a second force, such as provided by the inertia of the inner tube and inner tube cam 463 (coupled to the inner tube proximal portion), continues to apply a forward force to the proximal portion of the inner tube advancing it further in a distal direction. The action of the inner tube distal portion being depressed against the stepped surface of the outer cannula 430 causes the collapsible section to collapse. Because the tissue portion is in the inner tube interior, as the collapsible section collapses, the projecting section moves into the interior of the inner tube, engaging and sometimes severing the tissue portion. In one embodiment, the offset projecting sections of the flexible Nitinol collapsible section deflect inward in an "S" like action from an hour glass like shape that has been cut into the inner tube wall by a laser or other means in a manner to facilitate and influence this action. At a point, the collapsible section collapses no more and the proximal portion of the inner tube stops advancing. In some embodiments, the inner tube is kept in this position which maintains the projecting section's engagement of the tissue portion and the apparatus is pulled from the tissue taking with it the tissue portion. In some embodiments, the inner tube may extend back to its original, uncollapsed or neutral position and the severed tissue portion stays in the tube interior to be pulled from the tissue with the needle assembly 420 is withdrawn. In other embodiments, the knee like projecting section of the inner tube performs both the function of engaging or severing the specimen and holding the specimen in place while the needle assembly is removed.

The holder assembly 460 may also have a depth limiting stop that provides a set distance for the advancing of the outer cannula 430 into the tissue. This stop assists in providing a length of tissue portion to be withdrawn by the apparatus.

With the tissue portion engaged, the tissue portion is then withdrawn from the tissue. In one general embodiment, the step of withdrawing the tissue portion comprises withdrawing the needle assembly and the tissue portion from the tissue, applying a retrograde force on the collapsible section, disengaging the tissue portion and removing the tissue portion from the needle assembly.

To retrieve the tissue portion from the interior of the needle assembly 420 after the device is removed from the patient's tissue, the device is re-cocked in one embodiment. In some embodiments, this re-cocking simply pushes the tissue portion out of the inner tube. In other embodiments, this re-cocking relieves the forward force on the inner tube and the collapsible section allowing it to relax back into or near its normal shape of a fuller inner diameter and the tissue portion can then be removed. This cocking may be done with a handle that retracts the inner tube and the outer cannula 430 as well as set the trigger mechanism. In this embodiment, at a set point, the inner tube, outer cannula 430 and trigger mechanism are maintained in a set, ready configuration until the trigger button 469 is pushed. Once this set point is reached, the handle can be positioned back within the holder assembly 460. By reconfiguring the needle assembly 420 back into this ready configuration, the trigger mechanism is now ready to fire again. In one embodiment, the set point of the ready configuration, has the inner tube, outer cannula 420 and trocar tip positioned to repeat the tissue removal methods.

Operationally, as the device is being cocked, the inner tube and the outer cannula 430 are retracted back over the trocar needle 428 and the tissue portion is ejected by the action of the trocar needle 428 advancing relative to the inner tube, typically back to its ready configuration with the distal tip extending from the distal opening of the outer cannula 430.

Although this embodiment has the trocar maintaining its position with respect to the holder assembly, other embodiments having the trocar move relative to the holder assembly are possible.

In other embodiments of the methods of tissue removal, the apparatus is initially in an un-cocked configuration. In these embodiments, the apparatus is initially in an un-cocked position and, similar to the cocking methods above, the apparatus can be cocked to a ready configuration by putting a cocking force on a cocking element and the needle assembly can then be put into the ready configuration to repeatedly follow the tissue removal methods described.

Another example of a needle assembly in operation may be illustrated using the example embodiments of the needle assembly and tissue removal apparatus shown in FIGS. 7A-10B.

Referring again to the process steps shown in FIG. 11, the tissue removal apparatus is positioned in the tissue by manipulation of the holder assembly at 1180. This comprises providing the needle assembly configured in the ready configuration for triggering the needle assembly at 1182 and inserting the needle assembly into the tissue at 1184. This may be done manually be inserting the needle assembly into the tissue or by triggering the trigger mechanism which applies a forward force on the needle assembly and advances the assembly into the tissue. In this example embodiment, a forward force is applied to the latch handle which advances the latch key into the guide key ramp that deflects the guide keys and releases the slide and other elements of the needle assembly. As the needle assembly advances into the tissue, the tissue portion advances into the cavity of the inner tube and outer cannula. The tissue portion is engaged at 1185. In this embodiment, a forward force is applied to the inner tube at 1186 by applying a manual forward force to manually advance the inner tube cam. The force may also be applied automatically such as by the momentum of the inner tube and inner tube cam. A restraining force is applied to the outer cannula at 1187 by restricting the slide within the guide. These forces collapse the collapsible section at 1188 which has its proximal section welded to the distal portion of the exterior wall of the inner tube and its distal section welded to the interior of the outer cannula distal portion. The protruding section of the collapsible section engages the tissue portion with the inner tube and the outer cannula at 1189. At this point, the tissue section may be severed in the inner tube or it may be otherwise engaged in the needle assembly. It is understood that during these steps, the collapsible section may also be maintained in the collapsed position by mechanical means or by automatically or manually applying a forward force onto the inner tube. Additionally, a retrograde force may be applied to the inner tube changing the collapsed section from its collapsed position back to its neutral position. The tissue portion is withdrawn at 1190. In this embodiment, the apparatus, the needle assembly and the tissue portion are withdrawn at 1191 by manipulating the holder assembly to pull the needle assembly out of the tissue. At 1192, if not already done in preceding steps, a retrograde force is applied to the collapsible section. In this embodiment, this is done by applying a retrograde force on the inner tube handle and inner tube which is welded to the distal section of the collapsible section. The tissue portion is disengaged at 1193 when the collapsible section returns to its neutral position. The tissue portion may be removed at 1194 in this embodiment by advancing the plunger through the inner tube.

For embodiments of the needle assembly having the aperture, when the inner tube and collapsible section extend back to their uncollapsed or neutral position, non-sample portion material that has migrated under the collapsible section and become positioned between that and the outer cannula wall, may be expelled through the aperture and out of the outer cannula. This removal of non-sample material allows the collapsible section and the needle assembly to return to the neutral position, or to a position close to this neutral position. This closer position to the neutral position would not be possible if the non-sample portion were between the underside of the collapsible section and the interior cavity wall of the outer cannula.

In one embodiment, the needle assembly may be reconfigured into the ready configuration at 1195. This may be performed by cocking the needle assembly at 1196. With this embodiment, the assembly is cocked by putting a cocking force on a cocking element, here applying a retrograde force to pull the latch handle until the outer cannula and the slide are restrained by engaging the latch key and the latch at 1197. In some embodiments, the plunger may remain in one position and as the inner tube and the outer cannula are pulled back, the plunger may expel the tissue portion from the inner tube as the needle assembly moves to the ready configuration. At this point, the tissue removal assembly is in the ready configuration for possible reuse.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

We claim:

1. A needle assembly, the needle assembly comprising:
   an inner tube having an interior cavity;
   an outer cannula having a proximal portion, a distal portion and an interior cavity;
   the interior cavity of the outer cannula having an interior diameter to slidably receive the inner tube;
   a collapsible leg operably engaged with the inner tube and the outer cannula whereby a forward movement of a portion of the inner tube within the interior cavity of the outer cannula changes the collapsible leg from a neutral position to a collapsed position;
   an aperture extending through an interior cavity wall of the outer cannula; and
   the aperture configured to pass a tissue portion from the interior cavity of the outer cannula.

2. The needle assembly of claim 1 wherein the aperture is positioned under the collapsible leg when the inner tube and the collapsible leg are received in the interior cavity of the outer cannula.

3. The needle assembly of claim 1 wherein:
   the tissue portion comprises a non-sample portion and a sample portion; and
   the non-sample portion may be passed from the interior cavity of the outer cannula through the aperture and the sample portion may be retained in the interior cavity of the outer cannula.

4. The needle assembly of claim 1 wherein the tissue portion may be passed from under the collapsible leg through the aperture.

5. The needle assembly of claim 1 wherein the aperture is positioned under a pocket of the collapsible leg when the inner tube and the collapsible leg are received in the interior cavity of the outer cannula.

6. The needle assembly of claim 1 wherein an aperture shape of the aperture comprises one selected from the group consisting of:

a rectangle;
an oval; and
a rectangle with rounded edges.

7. The needle assembly of claim 1 wherein the collapsible leg comprises a separately manufactured element coupled to the inner tube.

8. The needle assembly of claim 1 wherein the collapsible leg is coupled to the distal portion of the inner tube by a first weld and the collapsible leg is coupled to the distal portion of the outer cannula by a second weld.

9. The needle assembly of claim 1 further comprising:
a first cam coupled to the proximal portion of the inner tube; and
a second cam coupled to the proximal portion of the outer cannula.

10. The needle assembly of claim 1 wherein the collapsible leg comprises an elastically collapsible leg.

11. The needle assembly of claim 1 wherein the needle assembly is configured to be reused to remove a plurality of tissue portions.

12. The needle assembly of claim 1 wherein the collapsible leg is formed from a super elastic material.

13. A method of using the needle assembly of claim 1, the method comprising:
providing the needle assembly of claim 1;
positioning the needle assembly in a tissue;
engaging the tissue portion in the tissue with the needle assembly; and
withdrawing the tissue portion from the tissue.

14. The method of claim 13 wherein the step of engaging the tissue portion in the tissue with the needle assembly further comprises:
applying a forward force to the inner tube;
applying a restraining force to the outer cannula; and
collapsing the collapsible leg whereby the collapsible leg engages the tissue portion in the inner tube.

15. A tissue removal assembly comprising:
an outer cannula having an interior cavity;
an inner tube slidably received in the outer cannula;
a collapsible section operably engage with the inner tube and the outer cannula whereby a forward force on the inner tube and a restraining force on the outer cannula collapses the collapsible section into a collapsed position; and
an aperture extending through an interior cavity wall of the outer cannula configured to pass a tissue portion from the interior cavity of the outer cannula.

16. The tissue removal assembly of claim 15 further comprising a holder assembly configured to provide the forward force on the inner tube and the restraining force on the outer cannula.

17. A method of using the tissue removal assembly of claim 15, the method comprising:
providing the tissue removal assembly of claim 15;
positioning the tissue removal assembly in a tissue;
engaging the tissue portion in the tissue with the tissue removal assembly; and
withdrawing the tissue portion from the tissue.

18. The method of claim 17 wherein the step of engaging the tissue portion in the tissue with the tissue removal assembly further comprises:
applying the forward force to the inner tube;
applying the restraining force to the outer cannula; and
collapsing the collapsible section whereby the collapsible section engages the tissue portion in the inner tube.

19. A needle assembly comprising:
an inner tube;
an outer cannula having an exterior wall, an interior cavity defined by an interior cavity wall;
an aperture extending through the interior cavity wall;
the outer cannula configured to slidably receive the inner tube;
a collapsible leg operably engaged with the inner tube and the outer cannula whereby a forward movement of a portion of the inner tube relative to the outer cannula changes the collapsible leg from a neutral position to a collapsed position; and
the aperture configured to expel a tissue portion from the interior cavity of the outer cannula through the aperture.

20. A method of using the needle assembly of claim 19, the method comprising:
providing the needle assembly of claim 19;
positioning the needle assembly in a tissue;
engaging the tissue portion in the tissue with the needle assembly; and
withdrawing the tissue portion from the tissue.

* * * * *